(12) United States Patent
Kapatoes et al.

(10) Patent No.: US 12,011,616 B2
(45) Date of Patent: *Jun. 18, 2024

(54) IMAGE-BASED RADIATION THERAPY QUALITY ASSURANCE

(71) Applicant: Sun Nuclear Corporation, Melbourne, FL (US)

(72) Inventors: Jeffrey M. Kapatoes, Melbourne, FL (US); Jeffery Simon, Indian Harbour Beach, FL (US); Kirolos Tadrous, Melbourne, FL (US); Jason McClasky, Cocoa, FL (US); Victor Price, Rockledge, FL (US); Ryan Wilson, Melbourne, FL (US)

(73) Assignee: Sun Nuclear Corporation, Melbourne, FL (US)

( * ) Notice: Subject to any disclaimer, the term of this patent is extended or adjusted under 35 U.S.C. 154(b) by 570 days.

This patent is subject to a terminal disclaimer.

(21) Appl. No.: 17/234,653

(22) Filed: Apr. 19, 2021

(65) Prior Publication Data

US 2021/0236856 A1    Aug. 5, 2021

Related U.S. Application Data

(63) Continuation-in-part of application No. 16/999,700, filed on Aug. 21, 2020, now Pat. No. 11,600,004,
(Continued)

(51) Int. Cl.
*A61N 5/10*    (2006.01)
*G06T 7/13*    (2017.01)

(52) U.S. Cl.
CPC ........ *A61N 5/1075* (2013.01); *A61N 5/1031* (2013.01); *A61N 5/1045* (2013.01); *G06T 7/13* (2017.01); *G06T 2207/30096* (2013.01)

(58) Field of Classification Search
CPC .. A61N 5/1075; A61N 5/1031; A61N 5/1045; A61N 2005/1076; A61N 5/1071;
(Continued)

(56) References Cited

U.S. PATENT DOCUMENTS 759,608 A    5/1904  Harper
1,239,145 A    9/1917  Wantz
(Continued)

FOREIGN PATENT DOCUMENTS

CA    2718408    9/2009
DE    102009039345 A1    3/2011
(Continued)

OTHER PUBLICATIONS

Albers et al., CRC HAndbook of Chemistry and Physics, 87th Ed., Edited by R.C. Weast CRC, Cleveland, 1976. pp. F-11, D-171, E-6. (4 pages).
(Continued)

*Primary Examiner* — Siamak Harandi
(74) *Attorney, Agent, or Firm* — Pillsbury Winthrop Shaw Pittman LLP

(57) ABSTRACT

Systems, methods, and computer software are disclosed for receiving a video stream and acquiring images capturing at least a portion of a shape representative of a radiation field generated by a radiation delivery system that includes a radiation source configured to deliver the radiation beam, the acquired images extracted from the video stream.

21 Claims, 20 Drawing Sheets

Related U.S. Application Data which is a continuation-in-part of application No. 16/925,205, filed on Jul. 9, 2020, now Pat. No. 11,378,700.

(60) Provisional application No. 62/872,646, filed on Jul. 10, 2019.

(58) Field of Classification Search
CPC .................. A61N 5/1065; G06T 7/13; G06T 2207/30096
See application file for complete search history.

(56) References Cited

U.S. PATENT DOCUMENTS

| | | |
|---|---|---|
| 2,818,510 A | 12/1957 | Verse |
| 3,033,985 A | 5/1962 | Petree |
| 3,267,728 A | 8/1966 | Solomons |
| 3,327,213 A | 6/1967 | Wald, Jr. |
| 3,394,258 A | 7/1968 | Schleiger |
| 3,433,953 A | 3/1969 | Sweet |
| 3,665,762 A | 5/1972 | Domen |
| 3,783,251 A | 1/1974 | Pavkovich |
| 3,790,794 A | 2/1974 | Murray |
| 3,978,336 A | 8/1976 | Roux |
| 3,980,885 A | 9/1976 | Steward |
| 4,058,832 A | 11/1977 | Vagi |
| 4,063,097 A | 12/1977 | Barrett |
| 4,107,531 A | 8/1978 | Garratt |
| 4,157,472 A | 6/1979 | Barrett |
| 4,312,224 A | 1/1982 | Domen |
| 4,450,440 A | 5/1984 | White |
| 4,455,609 A | 6/1984 | Inamura |
| 4,613,754 A | 9/1986 | Vinegar |
| 4,729,099 A | 3/1988 | Iverson |
| 4,765,749 A | 8/1988 | Bourgade |
| 4,777,442 A | 10/1988 | Rosenthal |
| 4,887,287 A | 12/1989 | Cobben |
| 5,099,505 A | 3/1992 | Seppi |
| 5,160,337 A | 11/1992 | Cosman |
| 5,262,649 A | 11/1993 | Antonuk |
| 5,388,142 A | 2/1995 | Morris |
| 5,394,452 A | 2/1995 | Swerdloff |
| 5,596,653 A | 1/1997 | Kurokawa |
| 5,602,892 A | 2/1997 | Llacer |
| 5,621,214 A | 4/1997 | Sofield |
| 5,622,187 A | 4/1997 | Carol |
| 5,627,367 A | 5/1997 | Sofield |
| 5,635,709 A | 6/1997 | Sliski |
| 5,640,436 A | 6/1997 | Kawai |
| 5,661,310 A | 8/1997 | Jones |
| 5,704,890 A | 1/1998 | Bliss |
| 5,712,482 A | 1/1998 | Gaiser |
| 5,873,826 A | 2/1999 | Gono |
| 5,988,875 A | 11/1999 | Gershfeld |
| 6,038,283 A | 3/2000 | Carol |
| 6,125,335 A | 9/2000 | Simon |
| 6,131,690 A | 10/2000 | Galando |
| 6,148,272 A | 11/2000 | Bergstrom |
| 6,175,761 B1 | 1/2001 | Frandsen |
| 6,207,952 B1 | 3/2001 | Kan |
| 6,257,552 B1 | 7/2001 | Crow |
| 6,261,219 B1 | 7/2001 | Meloul |
| 6,301,329 B1 | 10/2001 | Surridge |
| 6,322,249 B1 * | 11/2001 | Wofford ............... A61N 5/1049 378/65 |
| 6,345,114 B1 | 2/2002 | Mackie |
| 6,364,529 B1 | 4/2002 | Dawson |
| 6,398,710 B1 | 6/2002 | Ishikawa |
| 6,516,046 B1 | 2/2003 | Stephan |
| 6,535,574 B1 | 3/2003 | Collins |
| 6,535,756 B1 | 3/2003 | Simon |
| 6,552,347 B1 | 4/2003 | Dimcovski |
| 6,560,311 B1 | 5/2003 | Shepard |
| 6,594,336 B2 | 7/2003 | Nishizawa |
| 6,609,626 B2 | 8/2003 | Young |
| 6,609,826 B1 | 8/2003 | Fujii |
| 6,626,569 B2 | 9/2003 | Reinstein |
| 6,636,622 B2 | 10/2003 | Mackie |
| 6,648,503 B2 | 11/2003 | Tanaka |
| 6,712,508 B2 | 3/2004 | Nilsson |
| 6,788,759 B2 | 9/2004 | Op De Beek |
| 6,799,068 B1 | 9/2004 | Hartmann |
| 6,810,107 B2 | 10/2004 | Steinberg |
| 6,810,108 B2 | 10/2004 | Clark |
| 6,833,707 B1 | 12/2004 | Dahn |
| 6,839,404 B2 | 1/2005 | Clark |
| 6,853,702 B2 | 2/2005 | Renner |
| 6,888,919 B2 | 5/2005 | Graf |
| 6,904,119 B2 | 6/2005 | Oikawa |
| 6,904,125 B2 | 6/2005 | Van Dyk |
| 6,904,162 B2 | 6/2005 | Robar |
| 6,974,254 B2 | 12/2005 | Paliwal |
| 6,990,368 B2 | 1/2006 | Simon |
| 6,992,309 B1 | 1/2006 | Petry |
| 7,016,454 B2 | 3/2006 | Warnberg |
| 7,065,812 B2 | 6/2006 | Newkirk |
| 7,076,023 B2 | 7/2006 | Ghelmansarai |
| 7,098,463 B2 | 8/2006 | Adamovics |
| 7,116,749 B2 | 10/2006 | Besson |
| 7,125,163 B2 | 10/2006 | Eigler |
| 7,127,028 B2 | 10/2006 | Sendai |
| 7,127,030 B2 | 10/2006 | Tamegai |
| 7,142,634 B2 | 11/2006 | Engler |
| 7,193,220 B1 | 3/2007 | Navarro |
| 7,221,733 B1 | 5/2007 | Takai |
| 7,233,688 B2 | 6/2007 | Ritt |
| 7,234,355 B2 | 6/2007 | Dewangan |
| 7,298,820 B2 | 11/2007 | Nelson |
| 7,339,159 B2 | 3/2008 | Juh |
| 7,349,523 B2 | 3/2008 | Jenkins |
| 7,352,840 B1 | 4/2008 | Nagarkar |
| 7,371,007 B2 | 5/2008 | Nilsson |
| 7,386,089 B2 | 6/2008 | Endo |
| 7,420,160 B2 | 9/2008 | Delaperriere |
| 7,453,976 B1 | 11/2008 | Yin |
| 7,455,449 B2 | 11/2008 | Nishimura |
| 7,471,765 B2 | 12/2008 | Jaffray |
| 7,515,681 B2 | 4/2009 | Ebstein |
| 7,579,608 B2 | 8/2009 | Takahashi |
| 7,605,365 B2 | 10/2009 | Chen |
| 7,636,419 B1 | 12/2009 | Nelson |
| 7,668,292 B1 | 2/2010 | Bose |
| 7,734,010 B2 | 6/2010 | Otto |
| 7,750,311 B2 | 7/2010 | Daghighian |
| 7,766,903 B2 | 8/2010 | Blumenkranz |
| 7,773,723 B2 | 8/2010 | Nord |
| 7,778,383 B2 | 8/2010 | Koehler |
| 7,778,392 B1 | 8/2010 | Berman |
| 7,778,680 B2 | 8/2010 | Goode, Jr. |
| 7,782,998 B2 | 8/2010 | Langan |
| 7,945,022 B2 | 5/2011 | Nelms |
| 8,044,359 B2 | 10/2011 | Simon |
| 8,093,549 B2 | 1/2012 | Navarro |
| 8,130,905 B1 | 3/2012 | Nelms |
| 8,136,773 B2 | 3/2012 | Schmutzer |
| 8,147,139 B2 | 4/2012 | Papaioannou |
| 8,218,718 B1 | 7/2012 | Van Herk |
| 8,235,530 B2 | 8/2012 | Maad |
| 8,242,458 B2 | 8/2012 | Rinecker |
| 8,321,179 B2 | 11/2012 | Simon |
| 8,325,878 B2 | 12/2012 | McNutt |
| 8,430,564 B2 | 4/2013 | Simmons |
| 8,457,713 B2 | 6/2013 | Kagermeier |
| 8,474,794 B2 | 7/2013 | Liljedahl |
| 8,536,547 B2 | 9/2013 | Maurer |
| 8,541,756 B1 | 9/2013 | Treas |
| 8,605,857 B1 | 12/2013 | Renner |
| 8,632,448 B1 | 1/2014 | Schulte |
| 8,726,814 B1 | 5/2014 | Matteo |
| 8,794,899 B2 | 8/2014 | Cozza |
| 8,833,709 B2 | 9/2014 | Weng |
| 8,840,304 B2 | 9/2014 | Perez Zarate |
| 8,840,340 B2 | 9/2014 | Eisenhower |

(56) References Cited

U.S. PATENT DOCUMENTS

| | | | |
|---|---|---|---|
| 8,874,385 | B2 | 10/2014 | Takayanagi |
| 8,927,921 | B1 | 1/2015 | Nelms |
| 9,050,460 | B2 | 6/2015 | Hildreth |
| 9,097,384 | B1 | 8/2015 | Simon |
| 9,310,263 | B2 | 4/2016 | Thoen |
| 9,463,336 | B2 | 10/2016 | Nelms |
| 9,480,861 | B2 | 11/2016 | Kapatoes |
| 9,561,388 | B2 | 2/2017 | Hildreth |
| 9,586,060 | B2 | 3/2017 | Seuntjens |
| 9,750,955 | B2 | 9/2017 | McNutt |
| 9,895,557 | B2 | 2/2018 | Seuntjens |
| 10,099,067 | B2 | 10/2018 | Kapatoes |
| 10,413,754 | B2 | 9/2019 | Seuntjens |
| 10,755,823 | B2 | 8/2020 | Carette |
| 2001/0042841 | A1 | 11/2001 | Lyons |
| 2002/0077545 | A1 | 6/2002 | Takahashi |
| 2002/0080912 | A1 | 6/2002 | Mackie |
| 2003/0043879 | A1 | 3/2003 | Tanaka |
| 2003/0043960 | A1 | 3/2003 | Op De Beek |
| 2003/0138077 | A1 | 7/2003 | Lee |
| 2003/0231740 | A1 | 12/2003 | Paliwal |
| 2004/0066880 | A1 | 4/2004 | Oikawa |
| 2004/0068182 | A1 | 4/2004 | Misra |
| 2004/0096033 | A1 | 5/2004 | Seppi |
| 2004/0113094 | A1 | 6/2004 | Lyons |
| 2004/0120560 | A1 | 6/2004 | Robar |
| 2004/0158145 | A1 | 8/2004 | Ghelmansarai |
| 2004/0211917 | A1 | 10/2004 | Adamovics |
| 2004/0228435 | A1 | 11/2004 | Russell |
| 2004/0251419 | A1 | 12/2004 | Nelson |
| 2005/0013406 | A1 | 1/2005 | Dyk |
| 2005/0077459 | A1 | 4/2005 | Engler |
| 2005/0111621 | A1 | 5/2005 | Riker |
| 2006/0002519 | A1 | 1/2006 | Jenkins |
| 2006/0033044 | A1 | 2/2006 | Gentry |
| 2006/0184124 | A1 | 8/2006 | Cowan |
| 2006/0203964 | A1 | 9/2006 | Nyholm |
| 2006/0203967 | A1 | 9/2006 | Nilsson |
| 2006/0266951 | A1 | 11/2006 | Fritsch |
| 2007/0041497 | A1 | 2/2007 | Schnarr |
| 2007/0041499 | A1 | 2/2007 | Lu |
| 2007/0053492 | A1 | 3/2007 | Kidani |
| 2007/0071169 | A1 | 3/2007 | Yeo |
| 2007/0081629 | A1 | 4/2007 | Yin |
| 2007/0086577 | A1 | 4/2007 | Kobayashi |
| 2007/0172020 | A1 | 7/2007 | Nambu |
| 2007/0195930 | A1 | 8/2007 | Kapatoes |
| 2008/0031406 | A1 | 2/2008 | Yan |
| 2008/0049896 | A1 | 2/2008 | Kuduvalli |
| 2008/0049898 | A1 | 2/2008 | Romesberg, III |
| 2008/0091388 | A1 | 4/2008 | Failla |
| 2008/0103834 | A1 | 5/2008 | Reiner |
| 2008/0118137 | A1 | 5/2008 | Chen |
| 2008/0260368 | A1 | 10/2008 | Chang |
| 2008/0292055 | A1 | 11/2008 | Boone |
| 2008/0298553 | A1* | 12/2008 | Takahashi .............. G21K 1/046 378/152 |
| 2009/0003512 | A1 | 1/2009 | Pouliot |
| 2009/0003528 | A1 | 1/2009 | Ramraj |
| 2009/0067576 | A1 | 3/2009 | Maltz |
| 2009/0090870 | A1 | 4/2009 | Ahnesjo |
| 2009/0175418 | A1 | 7/2009 | Sakurai |
| 2009/0217999 | A1 | 9/2009 | Becker |
| 2009/0227841 | A1 | 9/2009 | Miyako |
| 2009/0250618 | A1 | 10/2009 | Simon |
| 2009/0252292 | A1 | 10/2009 | Simon |
| 2009/0326365 | A1 | 12/2009 | Goldenberg |
| 2010/0008467 | A1 | 1/2010 | Dussault |
| 2011/0022360 | A1 | 1/2011 | Simon |
| 2011/0051893 | A1 | 3/2011 | McNutt |
| 2011/0085716 | A1 | 4/2011 | Chefd Hotel |
| 2011/0096906 | A1 | 4/2011 | Langeveld |
| 2011/0158386 | A1 | 6/2011 | Payne |
| 2011/0204262 | A1 | 8/2011 | Pu |
| 2011/0210258 | A1 | 9/2011 | Black |
| 2011/0248188 | A1 | 10/2011 | Brusasco |
| 2011/0278444 | A1 | 11/2011 | Navarro |
| 2011/0306864 | A1 | 12/2011 | Zarate |
| 2012/0014618 | A1 | 1/2012 | Sun |
| 2012/0025105 | A1 | 2/2012 | Brown |
| 2012/0025826 | A1 | 2/2012 | Zhou |
| 2012/0230462 | A1 | 9/2012 | Robar |
| 2012/0292517 | A1 | 11/2012 | Izaguirre |
| 2012/0305793 | A1 | 12/2012 | Schiefer |
| 2012/0326057 | A1 | 12/2012 | Remeijer |
| 2013/0048869 | A1 | 2/2013 | Kominami |
| 2013/0048883 | A1 | 2/2013 | Simon |
| 2013/0258105 | A1 | 10/2013 | Jozsef |
| 2013/0303902 | A1 | 11/2013 | Smith |
| 2014/0016754 | A1 | 1/2014 | Sugiyama |
| 2014/0064445 | A1 | 3/2014 | Adler |
| 2014/0073834 | A1 | 3/2014 | Hildreth |
| 2014/0077098 | A1 | 3/2014 | Tachikawa |
| 2014/0094642 | A1 | 4/2014 | Fuji |
| 2014/0105355 | A1 | 4/2014 | Toimela |
| 2014/0237213 | A1 | 8/2014 | Gill |
| 2014/0250480 | A1* | 9/2014 | Koh .................... H04N 21/266 725/110 |
| 2014/0263990 | A1 | 9/2014 | Kawrykow |
| 2015/0080634 | A1 | 3/2015 | Huber |
| 2015/0087879 | A1 | 3/2015 | Nelms |
| 2015/0108356 | A1 | 4/2015 | Seuntjens |
| 2015/0124930 | A1 | 5/2015 | Verhaegen |
| 2015/0238778 | A1 | 8/2015 | Hildreth |
| 2015/0283403 | A1 | 10/2015 | Kapatoes |
| 2015/0309193 | A1 | 10/2015 | Kozelka |
| 2015/0327825 | A1 | 11/2015 | Suzuki |
| 2015/0352376 | A1 | 12/2015 | Wiggers |
| 2016/0067479 | A1 | 3/2016 | Marcovecchio |
| 2016/0136460 | A1 | 5/2016 | Baltes |
| 2016/0166857 | A1 | 6/2016 | Nelms |
| 2016/0287906 | A1 | 10/2016 | Nord |
| 2016/0310762 | A1 | 10/2016 | Ramezanzadeh Moghadam |
| 2016/0361568 | A1* | 12/2016 | Chappelow ............ G21K 1/046 |
| 2017/0021194 | A1 | 1/2017 | Nelms |
| 2017/0173367 | A1 | 6/2017 | Seuntjens |
| 2017/0177812 | A1 | 6/2017 | Sjölund |
| 2017/0225015 | A1 | 8/2017 | Thieme |
| 2017/0274225 | A1 | 9/2017 | Baecklund |
| 2018/0014798 | A1 | 1/2018 | Beckman |
| 2018/0028143 | A1 | 2/2018 | Wiggers |
| 2018/0028840 | A1 | 2/2018 | Simon |
| 2018/0140272 | A1 | 5/2018 | Ruchala |
| 2018/0185672 | A1 | 7/2018 | Ramezanzadeh Moghadam |
| 2018/0243586 | A1 | 8/2018 | Ramezanzadeh Moghadam |
| 2018/0250529 | A1 | 9/2018 | Seuntjens |
| 2018/0250531 | A1 | 9/2018 | Ansorge |
| 2019/0118002 | A1 | 4/2019 | Rosenwald |
| 2019/0298285 | A1 | 10/2019 | Rakic |
| 2020/0101327 | A1 | 4/2020 | Alquist |
| 2020/0253001 | A1 | 8/2020 | Nauditt |
| 2021/0011178 | A1 | 1/2021 | Kapatoes |
| 2021/0012507 | A1 | 1/2021 | Kapatoes |

FOREIGN PATENT DOCUMENTS

| | | |
|---|---|---|
| EP | 1060726 | 12/2000 |
| EP | 1060726 B1 | 6/2004 |
| EP | 2016445 | 1/2009 |
| EP | 2078537 A1 | 7/2009 |
| EP | 2117649 A2 | 11/2009 |
| EP | 2186542 | 5/2010 |
| EP | 2457237 | 5/2012 |
| EP | 2708919 A2 | 3/2014 |
| EP | 2865417 | 4/2015 |
| EP | 2904974 | 8/2015 |
| EP | 3074088 | 10/2016 |
| EP | 3075417 | 10/2016 |
| JP | 05154209 | 6/1993 |
| JP | 2003310590 A | 11/2003 |
| JP | 2008105882 | 5/2008 |
| JP | 2010215428 | 9/2010 |
| JP | 2010234521 | 10/2010 |
| JP | 202035449 | 3/2020 |

(56) References Cited

FOREIGN PATENT DOCUMENTS

| | | |
|---|---|---|
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 A | 12/2013 |
| WO | 2015024360 | 2/2015 |
| WO | 2015073899 | 5/2015 |
| WO | 2016172352 | 10/2016 |
| WO | 2016200463 | 12/2016 |
| WO | 2019157249 A | 8/2019 |

OTHER PUBLICATIONS

Almond et al. In "AAPM TG-51 Protocol for Clinical Reference Dosimetry of High Energy Photon and Electron Beams", Med. Phys. VI, 26, pp. 1847-1870, 1999.

Aspen Aerogels, Pyrogel.RTM. 2250 Datasheet (Aspen Aerogels, Inc., Northborough, 2010). 2 pages.

Berlyand et al., "Portable Calorimeter for Measuring Absorbed Doses of X-Rays and Electrons from Accelerators", translated from Izerite'naya Teknika, No. 11, Nov. 1991, pp. 56-58.

Boutillon in "Gap Correction for the Calorimetric Measurement of Absorbed Dose in Graphite with a 60Co Beam", Phys. Med. Biol., vol. 34, pp. 1809-1821, 1989.

Daures et al., "New Constant-Temperature Operating Mode for Graphite Calorimeter at LNE-LNHB", Physics in Medicine and Biology, vol. 50, 2005, No. pp. 4035-4052.

Daures et al., "Small section graphite calorimeter (CR10) at LNE-LNHB for measurement in small beams for IMRT", Metrologica, (Dec. 1, 2011), XP020229547, 5 pages.

Daures et al., "Small Section Graphite Calorimeter (GR-10) at LNE-LNHB for Measurements in Small Beams for IMRT Metrologia", vol. 49, No. 5, 2012, pp. S174-S178.

Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.

Domen, "Absorbed Dose Water Calorimeter", (Med. Phys., vol. 7, 1980, pp. 157-159).

Duane et al., "An Absorbed Dose Calorimeter for IMRT Dosimetry", Metrologia, vol. 49, No. 5, 2012, pp. S168-S173.

IAEA, TRS., "398. Absorbed Dose Determination in External Beam Radiotherapy: An International Code of Practice for Dosimetry based on Standards of Absorbed Dose to Water," Vienna International Atomic Energy Agency (2000). 242 pages.

J. Seuntjens and S. Duane, "Photon absorbed dose standards," Metrologia 46, S39-S58 (2009).

Kawrakow et al. In "The EGSnrc Code System: Monte-Carlo Simulation of Electron and Photon Transport" (Canadian National Research Center, NRC Report PIRS-701, 2006.

Mc Ewen at al., 'A Portable Calorimeter for Measuring Absorbed Dose in the Radiotherapy Clinic', Physics in Medicine and Biology, vol. 45, No. 12, Dec. 2000, pp. 3675-3691.

McDonald et al., "Portable Tissue Equivalent Calorimeter", Medical Physics, vol. 3, 2, Mar.-Apr. 1976, pp. 80-86.

McEwen et al., "Portable Graphite Calorimeter for Measuring Absorbed Dose in the Radiotherapy Clinic", Standards and Codes of Practice in Medical Radiation Dosimetry,IAEA-CN-96-9P,2002, pp. 115-121.

Miller, "Polystyrene Calorimeter for Electron Beam Dose Measurements", Radiation Physics Chemistry vol. 46, No. 4-6, Aug. 1995, pp. 1243-1246.

Myers et al., "Precision Adiabatic Gamma-Ray Calorimeter using Thermistor Thermometry", Review of Scientific Instruments, vol. 32, No. 9, Sep. 1961, pp. 1013-1015.

Nutbrown et. "Evaluation of Factors to Convert Absorbed Dose Calibrations in Graphite to Water for Mega-Voltage Photon Beams" (UK National Pysical Laboratory, NPL Report CIRM 37, 2000. 45 pages.

Ostrowsky et al., "The Construction of the Graphite Calorimeter GR9 at LNE-LNHB (Geometrical and technical considerations)", Report CEA-R-6184, 2008, 52 pages.

Owen et al "Correction for the Effect of the Gaps around the Core of an Absorbed Dose Graphite Calorimeter in High Energy Photon Radiation" (Phys. Med. Biol., vol. 36, pp. 1699-1704, 1991.

Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.

Petree et al., "A Comparison of Absorbed Dose Determinations in Graphite by Cavity Ionization Measurements and by Calorimetry", Journal of Research of the National Bureau of Standards—C. Engineering and Instrumentation. vol. 71 C, No. 1, Jan.-Mar. 1967, pp. 19-27.

Picard et al., "Construction of an Absorbed-Dose Graphite Calorimeter", Report BIPM-09/01' May 2009, 12 pages.

R. Alfonso et al., 'A new formalism for reference dosimetry of small and nonstandard fields,' Med. Phys. 35, 5179-5186 (2008).

Renaud et al., "Development of a graphite probe calorimeter for absolute clinical dosimetry", Med. Phvs., (Jan. 9, 2013), vol. 40, No. 2, p. 020701, XP012170941, 6 pages.

Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.

Ross et al. In "Water Calorimetry for Radiation Dosimetry" (Phys. Med. Biol., 1996, vol. 41, pp. 1-29).

S. Picard, D. T. Burns, and P. Roger, "Determination of the specific heat capacity of a graphite sample using absolute and differential methods," Metrologia 44, 294-302 (2007).

Sander et al., "NPL's new absorbed dose standard for the calibration of HDR 192Ir brachytherapy sources," Metrologia 49, S184-S188 (2012).

Seuntjens et al., Review of Calorimeter Based Absorbed Dose to Water Standards, Standards and Codes of Practice in Medical Radiation Dosimetry, IAEA-CN-96-3, 2002 p. 37-66.

Stewart in "The Development of New Devices for Accurate Radiation Dose Measurement: A garded Liquid Ionization Chamber and an Electron Sealed Water Calorimeter" Ph. D. Dissertation McGill University, 2007.

Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.

Witzani et al., "A Graphite Absorbed-Dose Calorimeter in the Quasi-Isothermal Mode of Operation", Metrologia, vol. 20, No. 3, 1984, pp. 73-79.

Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).

Brusasco, C, et al. 'A Dosimetry System for Fast Measurement of 3D Depth-dose Profiles in Charged-particle Tumor Therapy with Scanning Techniques.' Nuclear Instruments & Methods In Physics Research, Section—B: Beam Interactions With Materials and Atom 168.4 (2000): 578-92.

PCT App. No. PCT/US2015/024360; International Search Report and Written Opinion mailed Oct. 8, 2015; 13 page.

PCT App. No. PCT/US2015/024360; International Preliminary Report on Patentability Chapter I mailed Oct. 4, 2016; 9 pages.

Nelms, Benjamin. "Variation in External Beam Treatment, Plan Quality: An Inter-institutional Study of Planners and Planning Systems." Practical Radiation Oncology 2.4 (2012): 296-305.

PCT App. No. PCT/US2014/065808; International Search Report and Written Opinion mailed May 21, 2015; 9 pages.

PCT App. No. PCT/US2014/065808; International Preliminary Report on Patentability Chapter I mailed May 17, 2016; 7 pages.

Mackie et al., "Photon Beam Dose Computations", Proceedings of the 1996 AAPM Summer School, 1996. 36 pages.

(56) References Cited

OTHER PUBLICATIONS

PCT App. No. PCT/US2012/058345; International Search Report mailed Apr. 17, 2013; 3 pages.
Ahnesjo et al., "Calculation and Application of Point Spread Functions for Treatment Planning with High Energy Photon Beams", Acta. Oncol., 26, 49-56, 1987.
PCT App. No. PCT/US2012/058345; International Preliminary Report on Patentability Chapter I mailed Apr. 1, 2014; 5 pages.
PCT App. No. PCT/US2012/058345; International Written Opinion of the International Search Authority mailed Mar. 29, 2014; 4 pages.
Ahnesjo et al., "Dose calculations for external photon beams in radiotherapy", Phys. Med. Biol. 44, R99-R155 1999.
Ahnesjo, "Collapsed Cone Convolution of Radiant Energy for Photon Dose Calculation in Heterogeneous Media", Med. Phys. 16, 577-92, 1989.
Amanatides et al., "A Fast Voxel Traversal Algorithm for Ray Tracing", Eurographics '87, Conference Proceedings, 1987, 10 pages.
Liu et al., "Correcting kernel tilting and hardening in convolution/superposition dose calculations for clinical devergent and polychomatic photon beams", Med. Phys. 24, 1729-1741, 1997.
Lu et al., "Accurate convolution/superposition for multi-resolution dose calculation using cumulative tabulated kernels", Phys. Med. Biol. 50, 655-680, 2005.
Mackie et al., The Use of Comp. In Rad. Ther., 107-110 1987.
Mackie et al., "Generation of Photon Energy Deposition Kernels Using the EGS Monte Carlo Code," 1988, Phys. Med. Biol. 33, pp. 1-20.
Mackie et al., "A convolution method of calculating dose for 15-MVx rays", Med. Phys. 12, 188-196, 1985.
Mohan et al., "Energy and angular distributions of photons from medical linear accelerators", Med. Phys. 12, 592-597, 1985.
Otto, "Volumetric modulated arc therapy: IMRT in a single gantry arc", Med. Phys. 35, 310-317, 2008.
Papanikolaou et al., "Investigation of the convolution method for polyenergetic spectra", Med. Phys. 20, 1327-1336, 1993.
Williams, "Pyramidal Parametrics", SIGGRAPH Comput. Graph. 17, 3, 1-11, 1983.
Yan et al., "Adaptive radiation therapy", Phys. Med. Biol. 42, 123-132, 1997.
Yu, "Intensity-modulated arc therapy with dynamic multileaf collimation: an alternative to tomotherapy", Phys. Med. Biol. 40, 1435-1449, 1995.
PCT App. No. PCT/US2009/043341; International Search Report mailed Jan. 5, 2010. 3 pages.
PCT App. No. PCT/US2009/043341; Written Opinion of the International Search Authority mailed Nov. 8, 2010. 3 pages.
PCT App. No. PCT/US2009/043341; International Preliminary Report on Patentability Chapter I mailed Nov. 9, 2010. 4 pages.
PCT App. No. PCT/US2012/053440; International Search Report and Written Opinion mailed Mar. 26, 2014; 3 pages.
"Waterphantom Dosimetry"; Medical Physics, vol. 3, May/Jun. 1976; pp. 189.
Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the AAPM; Med. Phys. 35(9), Sep. 2008; pp. 4186-4215.
PCT App. No. PCT/US2010/042680; International Search Report mailed Jan. 27, 2011; 2 pages.
PCT App. No. PCT/US2010/042680; International Written Opinion mailed Jan. 23, 2012; 8 pages.
PCT App. No. PCT/US2010/042680; International Preliminary Report on Patentability Chapter I mailed Jan. 24, 2012; 9 pages.
EP2457237 Supplemental European Search Report and Written Opinion mailed Mar. 8, 2017; 10 pages.
PCT App. No. PCT/US2009/036775; International Search Report mailed Nov. 12, 2009; 2 pages.

PCT App. No. PCT/US2009/036775; International Preliminary Report on Patentability Chapter II and Written Opinion mailed Sep. 12, 2010; 12 pages.
EP2277353 Search Report mailed Jul. 21, 2017; 10 pages.
Benedick Fraass; "Quality Assurance for Clinical Radiotherapy Treatment Planning," Med Phys., 25(10), Oct. 1998; pp. 1773-1829.
G.J. Kutcher; "Comprehensive AQ for Radiation Oncology Report;" AAPM Radiation Therapy Committee Task Group 40; Med. Phys., 21; Apr. 1994; pp. 581-618.
MapCheck and EPIDose; www.sunnuclear.com; manufactured by Sun Nuclear Corp.; Melbourne,FL; 2010, 8 pages.
MapCALC; www.sunnuclear.com; manufactured by Sun Nuclear Corp.; Melbourne, FL; 2009, 2 pages.
Joseph O. Deasy; "A Computational Environment for Radiotherapy Research," Med. Phys. 30, (5), May 2003; pp. 979-985.
Robert M. Eisberg; "Fundamentals of Modern Physics," Chapter 9—Perturbation Theory; John Wiley & Sons; 1967; pp. 268-272.
Cyberknife; Cyberknife Systems; "The Standard of Radiosurgery", by Accuracy, Sunnyvale, CA; 2009; pp. 1-6.
"HI-ART"; www.tomotherapy.com; TomoTherapy, Madison, WI; 2007; pp. 1-8.
"Rapid Arc"; Varian Medical Systems, Inc., Palo Alto, CA; www.varian.com; 2007; pp. 1-8.
"VMAT"; Elekta,Ltd., Crawley UK; Document No. 4513 3710770; Oct. 8, 2008, 8 pages.
D.W.O. Rogers; "Montey Carlo Techniques in Radiotherapy," Physics in Canada, Medical Physics Special Issue, v. 58 #2; 2002; pp. 63-70.
T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 82(2); Feb. 2007; pp. 201-201.
PCT App. No. PCT/US2009/036917; International Search Report mailed Sep. 17, 2009. 2 pages.
PCT App. No. PCT/US2009/036917; Written Opinion mailed Sep. 12, 2010; 4 pages.
PCT App. No. PCT/US2009/036917; International Preliminary Report on Chapter II Patentability mailed Mar. 15, 2011. 3 pages.
PCT/US2017/044472; International Search Report and Written Opinion of the International Searching Authority, or the Declaration mailed Oct. 13, 17; 12 pages.
PCT App. No. PCT/US2012/053440; International Preliminary Report on Patentability Chapter I mailed Mar. 3, 2015; 8 pages.
PCT App. No. PCT/US2016/028664; International Preliminary Report on Patentability mailed Nov. 2, 2017; 5 pages.
PCT App. No. PCT/US2017/062608; International Search Report and Written Opinion mailed Feb. 22, 2018; 11 pages.
McEwen et al.; "A portable calorimeter for measuring absorbed dose in radiotherapy clinic"; Dec. 2000; Phys. Med. Biol., vol. 45; pp. 3675-3691.
McDermott et al.; "Replacing Pretreatment Verification with In Vivo EPID Dosimetry for Prostate IMRT"; International Journal of Radiation: Oncology Biology Physics, Pergamon Press, USA, vol. 67, No. 5, Mar. 28, 2007, pp. 1568-1577, XP022101268, ISSN: 0360-3016, DOI: 10.1016/J.IJROBP.2006.11.047.
Nelms, Benjamin et al.; "Evaluation of a Fast Method of EPID-based Dosimetry for Intensity-modulated Radiation Therapy"; Journal of Applied Clinical Medical Physics, Jan. 1, 2010, pp. 140-157, XP055476020.
PCT App. No. PCT/US2018/020320; International Search Report and Written Opinion mailed Jul. 24, 2018; 18 pages.
Linacre, J.K. , "Harwell Graphite Calorimeter", IAEA, vol. 47, 1970 (pp. 46-54.).
PCT App. No. PCT/US2018/020320; International Preliminary Report on Patentability Chapter I mailed Sep. 12, 2019. pp. 1-11.
PCT Appl. No. PCT/US2018/056568; International Preliminary Report on Patentability, mailed Apr. 30, 2020. 8 pages.
Office Action dated Jun. 26, 2020 for U.S. Appl. No. 15/908,538 (pp. 1-15).

(56) References Cited

OTHER PUBLICATIONS

Notice of Allowance dated Sep. 2, 2020 for U.S. Appl. No. 16/846,227 (pp. 1-8).
International Search Report and Written Opinion mailed Oct. 2, 2020, PCT Application No. PCT/ US2020/041458.
Office Action dated Nov. 16, 2020 for U.S. Appl. No. 16/164,637 (pp. 1-8).
Notice of Allowance dated Dec. 23, 2020 for U.S. Appl. No. 15/908,538 (pp. 1-11).
Office Action dated Feb. 25, 2021 for U.S. Appl. No. 16/164,637 (pp. 1-14).
International Search Report and Written Opinion mailed Nov. 24, 2021, PCT Application No. PCT/IB2021/057573.
International Search Report and Written Opinion mailed Sep. 1, 2023, PCT Application No. PCT/iB/2023/055991.
Barthe J Ed—Braucher Régis et al: "Electronic dosimeters based on solid state detectors", Nuclear Instruments & Methods in Physics Research. Section B: Beam Interactions With Materials and Atoms, Elsevier BV, NL, vol. 184, No. 1-2, Sep. 1, 2001 (Sep. 1, 2001), pp. 158-189, XP004306665, ISSN: 0168-583X (01) 00711-X.

\* cited by examiner

IMAGE-BASED RADIATION THERAPY QUALITY ASSURANCE

RELATED APPLICATION(S)

This application is a continuation-in-part of and claims priority to and the benefit of U.S. patent application Ser. No. 16/999,700, filed Aug. 21, 2020, which is a continuation-in-part of and claims priority to and the benefit of U.S. patent application Ser. No. 16/925,205, filed Jul. 9, 2020, titled "Scintillator-Based Radiation Therapy Quality Assurance," which claims priority to U.S. Provisional Application No. 62/872,646, filed Jul. 10, 2019, titled "Scintillator-Based Radiation Therapy Quality Assurance," the disclosures of which are hereby incorporated by reference.

DESCRIPTION OF THE RELATED ART

Radiation therapy can be utilized in the treatment of diseases, for example, by delivering a dose of radiation to kill or to inhibit growth of a cancerous tumor. Devices to deliver radiation therapy can include, for example, radio-isotopes, heavy ion accelerators and linear accelerators that generate a photon beam directed at a tumor site. To irradiate a tumor while minimizing exposure to nearby healthy tissues, a radiation beam can be shaped by a collimating device, for example, a multileaf collimator (MLC). Multileaf collimators include a number of movable leaves that can be positioned to create a shaped aperture (e.g., shaped the same as the tumor, from the vantage point of the radiation beam).

Radiation therapy quality assurance can be performed to verify the proper operation of one or more components of a radiation therapy delivery system, for example, verifying the positioning of MLC leaves.

SUMMARY

Systems, computer program products, and methods are disclosed for determining a shape of a radiation field generated by a radiation delivery system that includes a radiation source configured to deliver a radiation beam. An implementation of a system and/or computer program product that determines the shape of the radiation field includes a non-transitory, machine-readable medium storing instructions which, when executed by at least one programmable processor, cause the at least one programmable processor to perform operations comprising: acquiring images capturing at least a portion of a shape representative of a radiation pattern generated by a radiation delivery system that includes a radiation source configured to deliver the radiation beam.

In some variations, a video stream can be received and acquiring of the images can be performed by extracting the images from the video stream.

In other variations, a video encoder can receive a digital video signal output from a radiation detector. The video encoder can convert the digital video signal output the video stream.

In other variations, a recorded video stream can be generated from the received video stream, where the acquired images are obtained from the recorded video stream.

In yet other variations, the video stream can be analyzed to determine when the patient changes and thereby determine the start and end points of the recorded video stream.

Also, in some variations, the operations can include applying an edge detection algorithm to a radiation pattern present in the images, the edge detection algorithm determining at least one edge of the radiation pattern corresponding to a leaf of a multi-leaf collimator; and determining a leaf position based at least on a location of the determined edge. The operations can also include comparing the leaf position with a planned leaf position, the comparing utilized in radiation therapy quality assurance.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Radiation therapy quality assurance is a field that includes, among other things, determining whether a radiation delivery system is functioning properly and providing the prescribed radiation dose to a patient as detailed in a radiation therapy treatment plan. While many radiation delivery systems include their own functionality for displaying output and diagnostic metrics, radiation therapy quality assurance products can obtain independent measurements of what the radiation delivery system is providing.

As used herein, the term "radiation delivery system" can include various components needed to generate, direct and control a radiation therapy beam. For example, a radiation therapy system can include a radiation source (e.g. a linear accelerator, particle beam source, etc.), a gantry (fixed or rotating), a collimator (to shape the radiation reaching the patient), imaging equipment (to image prior to or during therapy), and the like.

As part of quality assurance, the operation of various components of the radiation delivery system can be independently assessed. Examples of such operations can include, for example, verifying the output of the radiation source, the position of a rotating gantry, the configuration of a multileaf collimator (e.g., determining its leaf positions), etc. The present disclosure describes, among other things, systems, software, and methods for determining collimator configurations based on the analysis of radiation patterns that emerge after a radiation beam passes through the collimator.

Figure 1A:
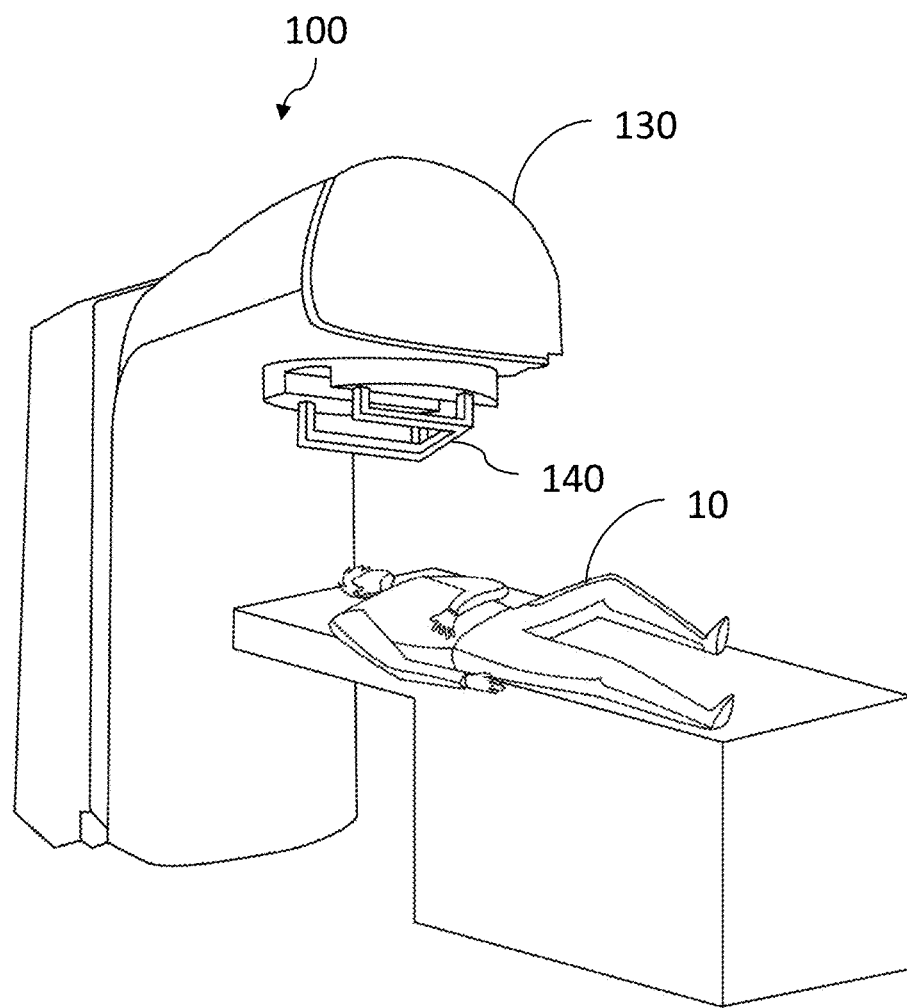
FIG. 1A is a diagram illustrating a perspective view of a simplified exemplary radiation delivery system in accordance with certain aspects of the present disclosure.
Figure 1B:
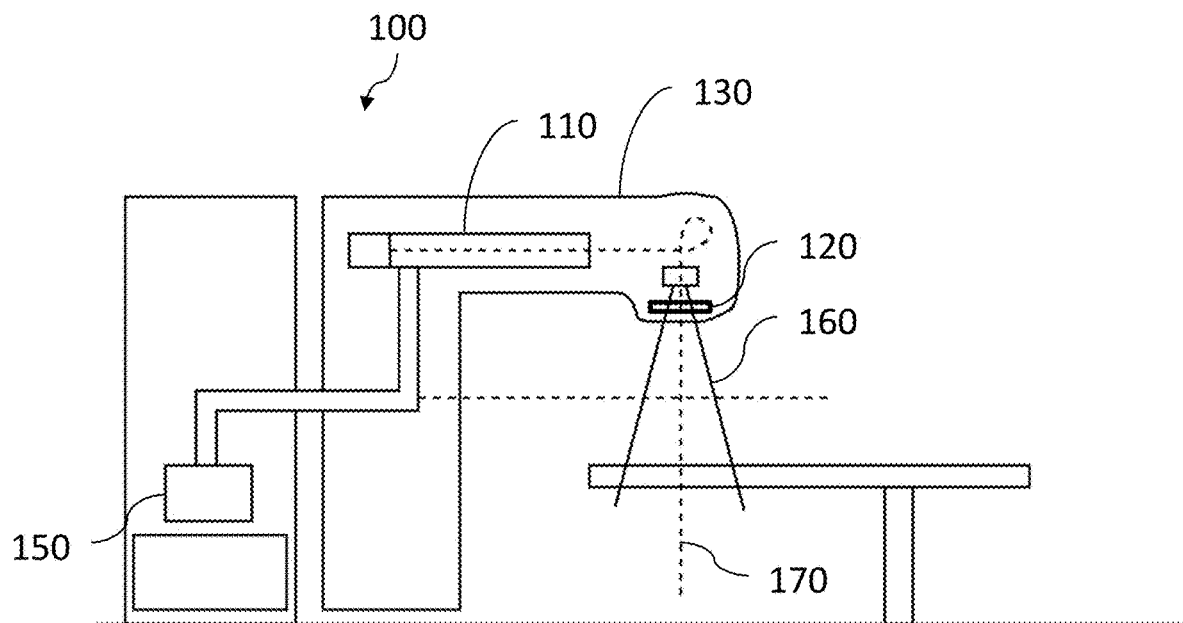
FIG. 1B is a diagram illustrating a side-sectional view of the simplified exemplary radiation delivery system of FIG. 1A in accordance with certain aspects of the present disclosure.

FIGS. 1A and 1B depict an exemplary radiation delivery system 100. This exemplary system is an open (or "C-arm") type system that includes a linear accelerator (e.g., element 110 in FIG. 1B) working with an RF source 150, a multileaf collimator 120, and a rotatable gantry 130. In this exemplary system, the linear accelerator and multileaf collimator are mounted within the rotatable gantry to allow radiation beam 160 to be delivered along beam axis 170 to a patient 10 at multiple angles. FIG. 1A also depicts an accessory tray 140 that can permit the mounting or positioning of hardware or devices between the radiation source and the patient. As described further herein, the technologies of the present disclosure can be used with radiation delivery systems such as the exemplary system depicted in FIGS. 1A and 1B, as well as with other types of radiotherapy systems.

Figure 2:
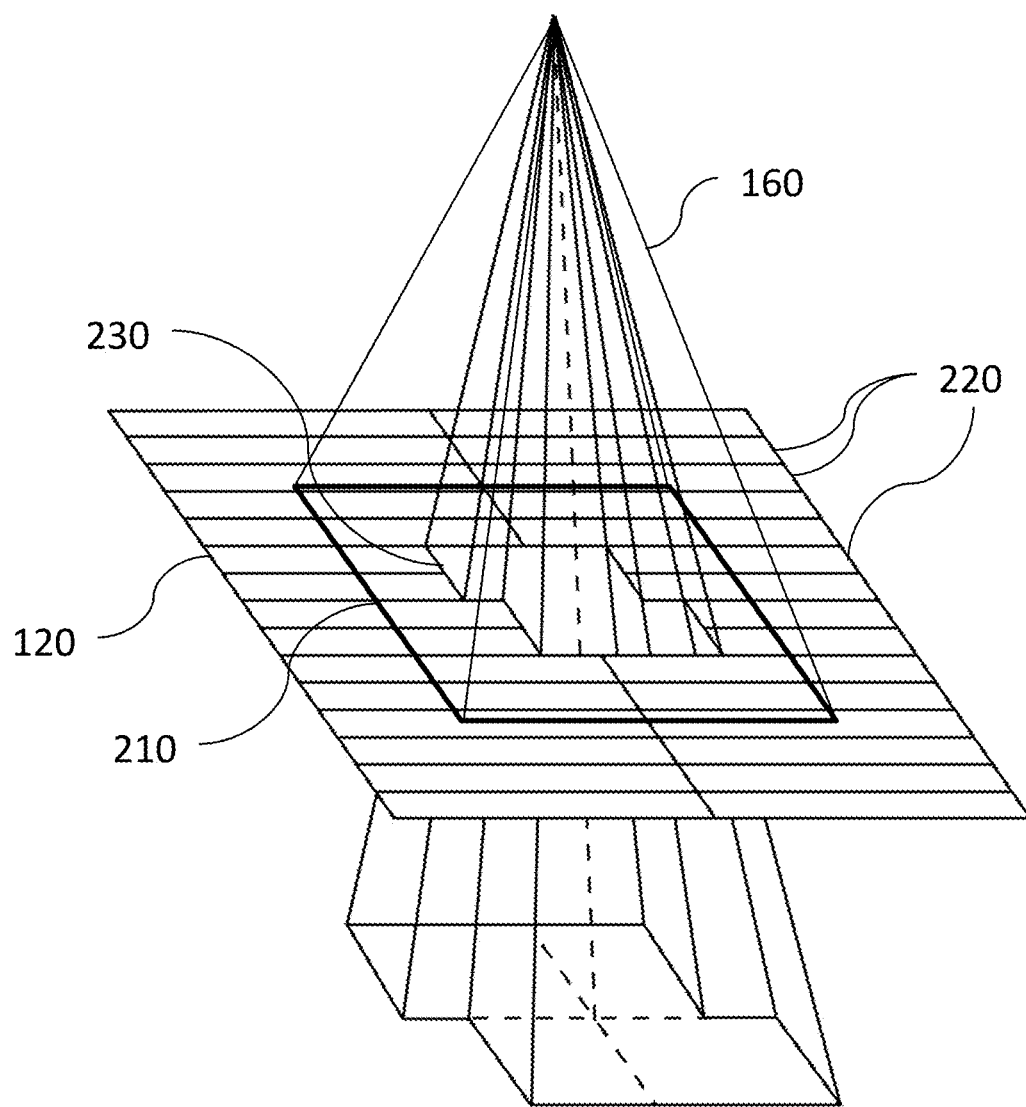
FIG. 2 is a diagram illustrating a perspective view of a simplified exemplary multileaf collimator shaping a radiation field in accordance with certain aspects of the present disclosure.

When performing radiation therapy quality assurance, one element of the radiation therapy device that can be assessed is the multileaf collimator (e.g., through verifying the collimator's leaf positions). One method for MLC configuration verification may involve examining the shape of the radiation field delivered to the patient by a radiation delivery system 100 including a radiation source (e.g., linear accelerator 110) configured to deliver a radiation beam 160. As shown in the simplified example of FIG. 2, a radiation field 210 can be shaped by blocking some portions with the leaves 220 of a multileaf collimator 120 to form an aperture 230. The portion of the radiation field that passes through the aperture will then proceed to the patient to deliver a dose of radiation in the desired shape. As used herein, the term "radiation field" can refer to radiation before or after being shaped by a collimator.

Scintillating materials may be used to determine the shape of a radiation field emerging from a multileaf collimator. "Determining the shape" can include determining the overall shape, determining particular MLC leaf positions (which provides information regarding the shape), etc.

"Scintillators," as discussed herein, are understood to include any material that, when hit by radiation, emit radiation (e.g., particle or photon) that can be detected (for example, by a camera). Scintillators include materials that absorb incoming radiation and then re-emit a portion of the absorbed energy in the form of light. It should be noted that when the term "light" is used herein, it is intended to include radiation within, or not within, the visible spectrum (for example, scintillators that emit infrared or other types of radiation are contemplated). Examples of scintillators can include plastic scintillators (such as Li6 plastic scintillators or polyethylene naphthalate), luminophores, crystal scintillators, phosphorescent materials, etc. As used herein, a "camera" can be any device that can detect radiation (e.g., light) coming from a scintillator. Examples of cameras can include CCD cameras, photodiodes, photomultiplier tubes, etc.

Figure 3:
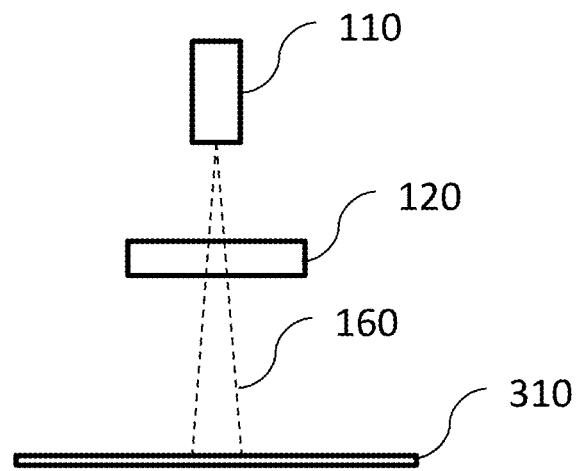
FIG. 3 is a diagram illustrating views of a simplified exemplary radiation pattern at a scintillator in accordance with certain aspects of the present disclosure.
Figure 3:
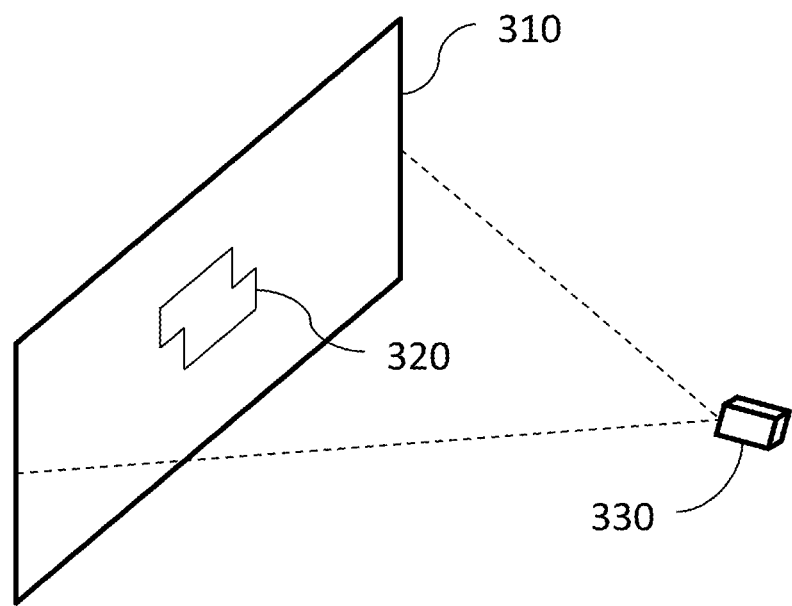

The top portion of FIG. 3 illustrates a simplified example of a scintillator 310 receiving a radiation beam 160 from radiation delivery system 110, after it passes through a multileaf collimator 120.

The lower portion of FIG. 3 illustrates a simplified example of a system for detecting a radiation pattern 320 from scintillator 310 using a camera 330. The radiation pattern 320 is related to the shape of the aperture formed by the multileaf collimator (as used herein, "radiation pattern" refers to the pattern present at the scintillator as it emits radiation/light after exposure to a radiation field).

Analysis of the images or signals acquired by the camera from the scintillator's radiation patterns can provide estimates of leaf positions of the multileaf collimator, independent of leaf position information that may be provided by the radiation delivery system itself.

Figure 3A:
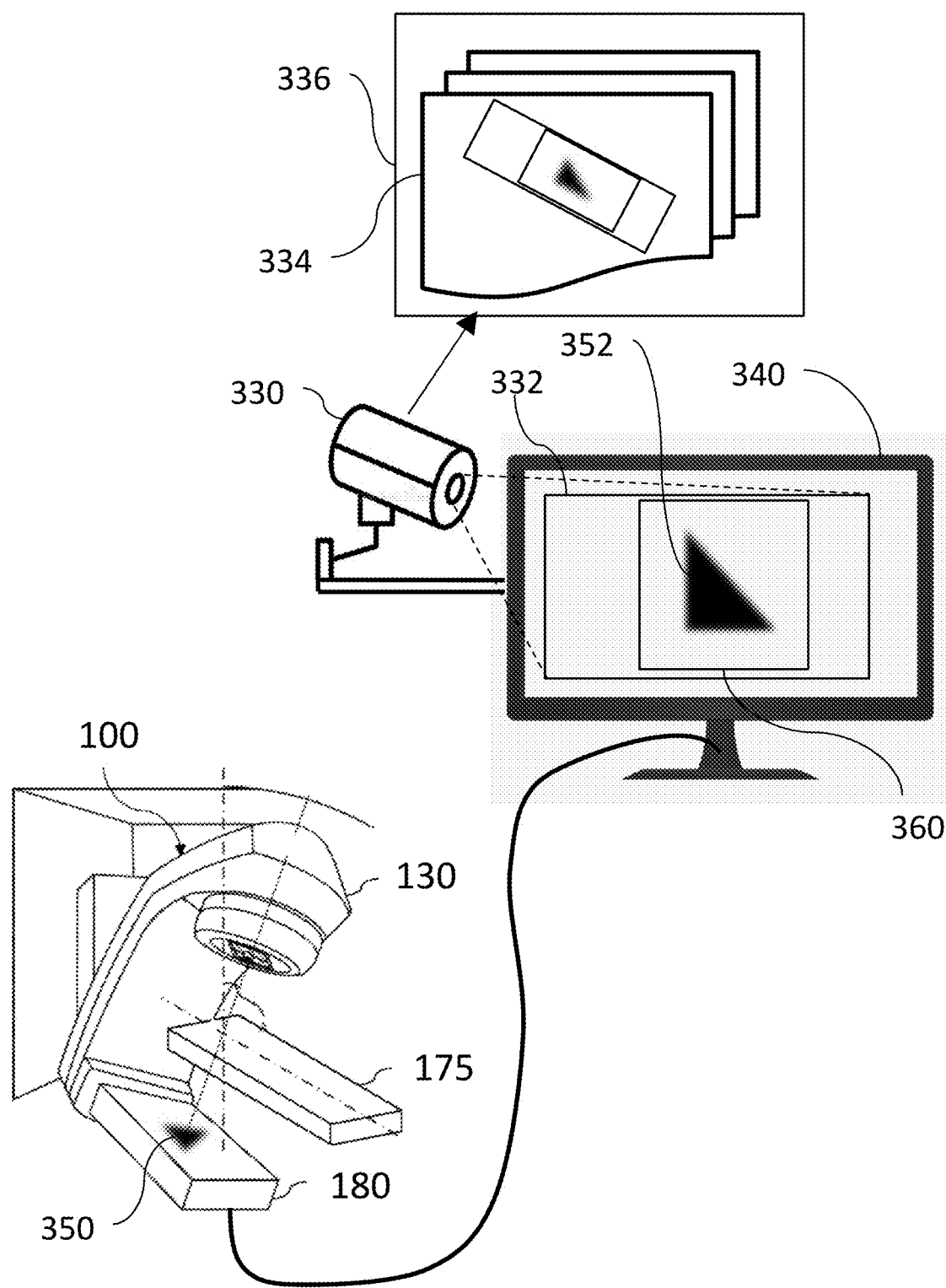
FIG. 3A is a diagram illustrating an exemplary system utilizing a camera to capture images of a radiation pattern displayed on a computer monitor in accordance with certain aspects of the present disclosure.

With reference to FIG. 3a, the disclosure herein relating to obtaining and utilizing a shape of a radiation pattern at a scintillator also applies to obtaining images by, for example, using a camera 330 or screen capturing software to obtain images from a computer monitor 340 displaying information from a radiation detector 180 (e.g., an EPID). Camera 330 can have a field of view 332, which may be different than the extents of the computer monitor. As used herein, and depicted in FIG. 3a, the captured images (e.g., a video file generated by the camera or screen capture software) are referred to as images 334 and can be processed by image processing module 336.

During treatment or quality assurance, personnel may observe at computer monitor 340 the radiation pattern 350 at the radiation detector 180 in terms of an accumulated amount of radiation. Such monitors can display the shape 352 of the radiation pattern at any resolution (i.e., possibly, but not necessarily, the same resolution as the active surface of the radiation detector). For example, the radiation detector could have 1000×2000 detector elements but displayed at the computer monitor with 2000×4000 pixels, thus corresponding to four pixels at the computer monitor per detector element at the radiation detector. In some implementations, to provide a reference as to the extent of the displayed computer monitor image, the computer monitor may display a bounding box 360 of known size, scale, or other indication of the actual size of the radiation pattern at the radiation detector. Also, the shape can be displayed to also communicate the intensity of radiation. For example, the shape can have pixels with different colors reflecting different intensities or accumulations of radiation. As described further herein, tilted scintillators, computer monitors, or analysis of video streams from the radiation detector can be utilized to provide information about the radiation reaching the radiation detector, with such information usable to derive collimator positions, dose calculation, fluence maps, etc.

The present disclosure describes, among other things, technologies utilizing scintillators to verify collimator leaf positions. However, contrary to what is common in the art, the present disclosure describes certain embodiments that utilize a scintillator that is tilted, so as to not be perpendicular to the axis of the radiation beam. Also contrary to the art, certain embodiments disclose a scintillator system with a very shallow angle between the camera and the scintillator. For example, disclosed systems may be configured such that the angle between a planar scintillator and the camera's line of sight is less than 10 degrees.

Figure 4:
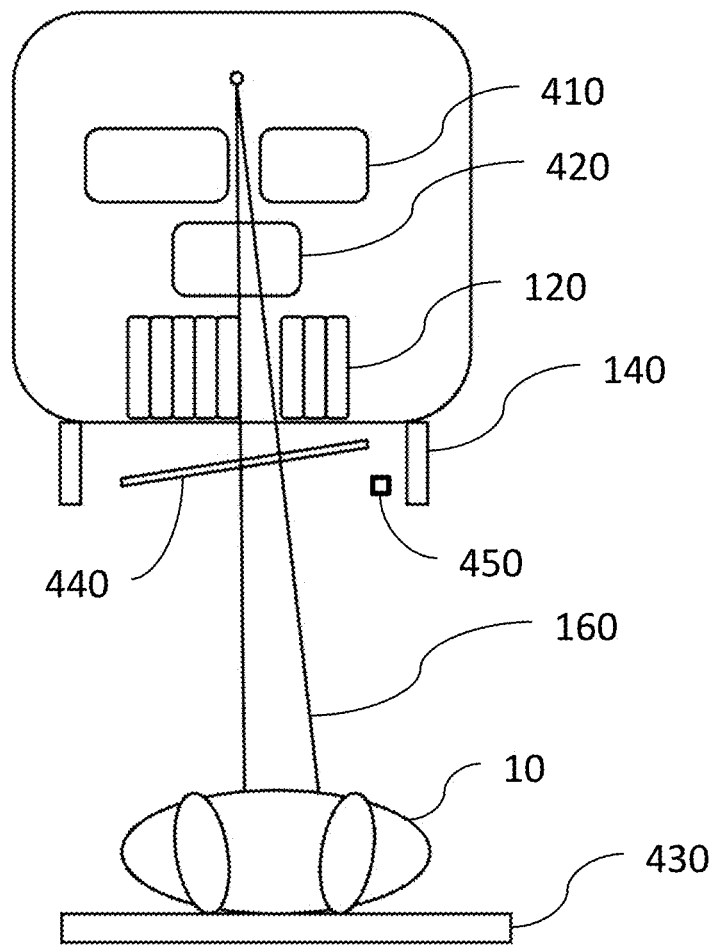
FIG. 4 is a diagram illustrating an end-perspective view of a simplified exemplary scintillator fixed in an orientation that is not perpendicular to the radiation beam axis in accordance with certain aspects of the present disclosure.

One implementation of the disclosed technology for determining at least a portion of a shape of a radiation field is depicted in FIG. 4. The figure illustrates a simplified representation of a radiation source 402 and a series of collimators (an X-axis jaw 410, a Y-axis jaw 420, and a multileaf collimator 120). Also illustrated is a patient 10 lying on a couch 430 such that the patient is hit by radiation beam 160 after its passes through the collimators. An accessory tray 140 is also depicted between the collimators and the patient couch.

The exemplary system of FIG. 4 can also include a scintillator 440 and a camera 450 configured to acquire images of light emitted by the scintillator during delivery of the radiation beam. As shown in FIG. 4, the scintillator and camera system can be configured to be located between the radiation source and a patient couch, thus functioning as an entrance detector.

It is contemplated that scintillator 440 may include a planar sheet of scintillating material or may include a curved sheet of scintillating material that may, for example, be oriented to have its convex surface facing toward the camera. In some embodiments, scintillator 440 may be sized to be large enough to cover the largest radiation field the radiation delivery system can deliver (at the location of the scintillator). In other embodiments, scintillator 440 may be more compact and may be smaller than the largest radiation field the system can deliver at the location of the scintillator, yet still sufficient for performing some measure of quality assurance.

Figure 5A:
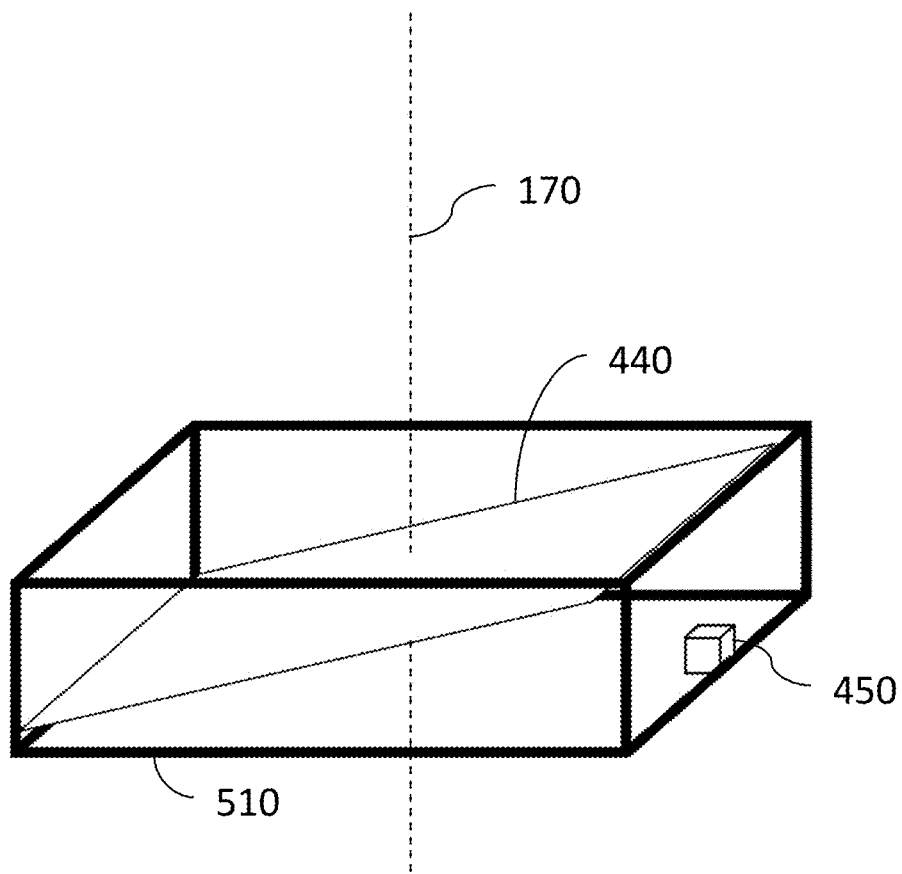
FIG. 5A is a diagram illustrating a perspective view of a simplified exemplary scintillator and camera fixed in a supporting structure in accordance with certain aspects of the present disclosure.

As illustrated in FIG. 5A, scintillator 440 and camera 450 can be fixed in a support structure 510. The support structure 510 may then be configured to be mounted to a radiation delivery system so that the scintillator will be struck by the radiation treatment beam.

The scintillator and camera are preferably fixed to the support structure in a manner that sets a specific desired geometric relationship between the scintillator and camera. The exemplary embodiment depicted in FIG. 5A illustrates a simplified framework where the scintillator is located within the support structure and the camera is located and configured to view one side of the scintillator (e.g., its bottom surface). It is contemplated, however, that the camera may be placed in a position to view the top surface of the scintillator or that more than one camera may be used.

In some embodiments, the scintillator and camera can be fixed to the support structure so that when the support structure is mounted to the radiation delivery system, the scintillator is not perpendicular to an axis of the radiation beam. FIG. 4 illustrates such an example of a scintillator 440 not being perpendicular to the axis 170 of radiation beam 160. When referring herein to a scintillator being oriented so that it is not perpendicular to an axis of the radiation beam, such refers to an orientation that is purposefully not perpendicular (i.e., as opposed to an orientation that may slightly deviate from an intended perpendicular positioning).

Some embodiments may have the scintillator fixed to the support structure so that the scintillator will be at an angle of between 80 to 89 degrees or between 91 and 110 degrees relative to the axis of the radiation beam when the support structure is mounted to the radiation delivery system. In other embodiments, the scintillator can be at an angle of between 84 and 88 degrees or between 92 and 96 degrees relative to the axis of the radiation beam when the support structure is mounted to the radiation delivery system. While the exemplary embodiment depicted in FIG. 4 shows a tilt in the Y direction, it is contemplated that a similar tilt could be implemented in the X direction or in both the X and Y directions.

In some embodiments, such as the one depicted in FIG. 5A, camera 450 and scintillator 440 can be fixed to support structure locations that maximize the angle between the camera and the scintillator. In such examples, the camera may be at one end of the support structure, as depicted, or may be in a corner of the support structure, or may even be located outside the perimeter of the support structure. Such embodiments can be beneficial in that the resolution of the radiation pattern imaged by the camera can be increased as compared to smaller angles where the radiation pattern is viewed more edge-on.

The design of the support structure can be substantially open above and/or below the scintillator to reduce or eliminate material that may attenuate the radiation therapy beam. Alternatively, the scintillator and the camera can be substantially enclosed by the support structure (for example, to prevent dust from accumulating on the scintillator or to protect it from damage or scratching). In such embodiments, the top portion and/or bottom portion of the support structure may be designed to provide only minimal attenuation of a radiation beam. For example, the top and/or bottom portion may be a layer of thin plastic or glass that causes only slight attenuation of the radiation beam.

The example depicted in FIG. 5A can represent a support structure 510 that substantially encloses the scintillator (i.e., is closed on all sides), but FIG. 5A is also intended to depict an example where the support structure 510 is merely a frame for mounting the scintillator and camera—with all the sides and the top/bottom being open.

Figure 5B:
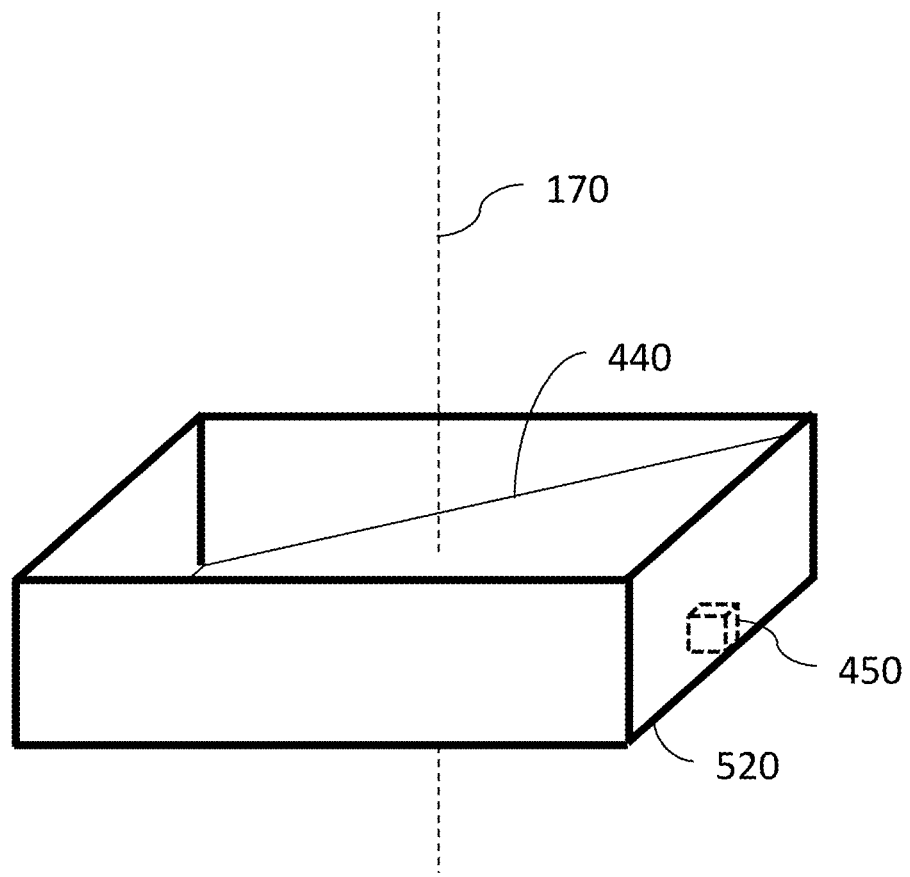
FIG. 5B is a diagram illustrating a perspective view of a simplified exemplary scintillator and camera fixed in a supporting structure that is open on a top and bottom portion in accordance with certain aspects of the present disclosure.

FIG. 5B Illustrates another exemplary embodiment in which the top portion and bottom portion of support structure 520 are open to allow light or other radiation unobstructed access to/through the scintillator, but where the support structure 520 also includes closed structural portions on its sides.

The present disclosure contemplates support structures that are constructed to include any combination of open or closed or transparent/translucent top, bottom or side materials.

Some embodiments of the present disclosure can enable the use of a visible light source (e.g., a tungsten or any sort of atomic lamp, or a white light source) to check the shape of a collimator aperture while the scintillator/support structure is in place. In such embodiments, the support structure can include translucent or transparent portions, which may be, for example, the top portion, bottom portion, or any portion(s) that form the sides of the support structure. It is contemplated that any combination of portions of the support structure may be translucent or transparent. Similarly, the scintillator may also be translucent or transparent. Such translucent or transparent support structure portions and/or scintillators can allow formation of a pattern at a target location (e.g., at the isoplane) corresponding to the shape of a collimator aperture when a light source shines light through the collimator aperture onto the scintillator and/or supporting structure portion. The present disclosure contemplates that any embodiments herein (not just planar scintil-lator embodiments) can incorporate transparent or translucent support structure portions and/or scintillators.

As used herein, the term "transparent" means that light corresponding to the shape of the collimator aperture is able to pass through without significant distortion, resulting in a pattern that can be accurately related to the shape of the collimator aperture. Similarly, as used herein, the term "translucent" means that light is able to pass, but there may be some distortion or dimming of the light and the resulting pattern corresponding to the shape of the collimator aperture. In embodiments where a translucent material is used, it is contemplated that degree of distortion will not be prohibitive of providing a pattern that can be utilized in radiation therapy quality assurance for determining the shape of a collimator aperture. Also, it is contemplated that the transparent or translucent material described herein can have any degree of attenuation of light. For example, a transparent scintillator may attenuate 50% of light but still allow a sharp (though dimmer) pattern to be formed at the target location. According to the type of application desired, translucent or transparent scintillators can have a polyvinyltoluene base, optionally including some fraction of lead (e.g., approximately 2%—appropriate for x-ray dosimetry), etc.

In some embodiments, the support structure can be configured to be mounted to the radiation delivery system at an accessory tray disposed between the radiation source and a patient couch. For example, a linear accelerator may have an accessory tray or slot into which the support structure may be mounted. It thus contemplated herein that when reference is made to a support structure being "configured to be mounted," this can include, for example, being configured in a way to be removably mounted (e.g., structurally designed to slide into an accessory tray slot or specifically sized to fit within the tray). Support structures herein are also contemplated to be configured to be mounted by virtue of more permanent structures such as the provision of screw holes or other fastening accessories to aid in mounting to a particular portion of a radiation delivery system.

In certain embodiments, the scintillator(s) and camera(s) can be fixed to the support structure in a manner so that the whole assembly fits entirely within an accessory tray.

The support structure mounting, in conjunction with specific fixation therein of the scintillator and camera can result in a tilted scintillator orientation with regard to the axis of the radiation beam. For example, mounting the support structure into a linac accessory tray that is perpendicular to the axis of the radiation beam, when the scintillator is fixed at an angle within the supporting structure, results in the scintillator being tilted with regard to the axis of the radiation beam.

Figure 6:
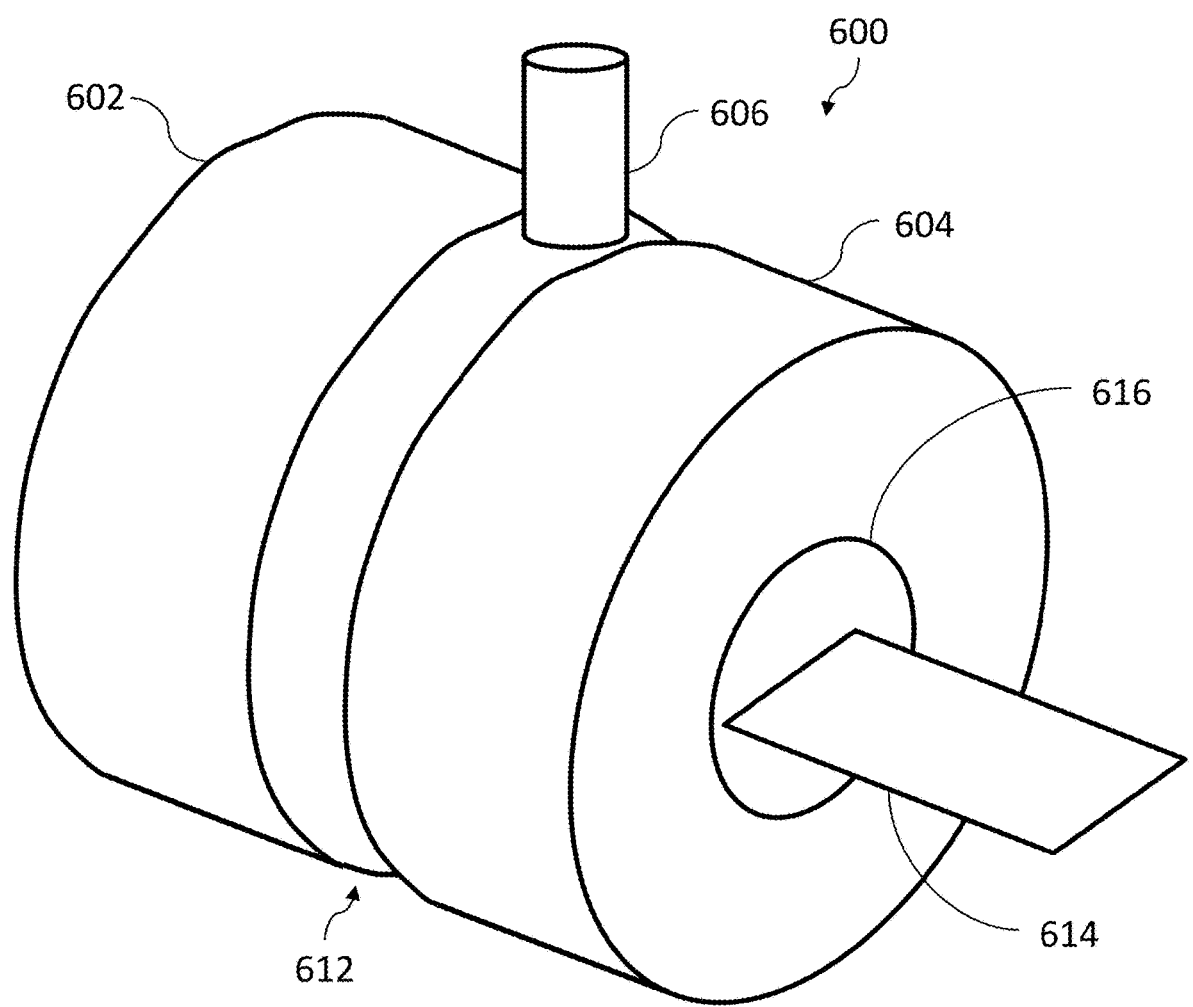
FIG. 6 is a diagram illustrating a perspective view of a simplified exemplary combined radiotherapy and medical imaging system in accordance with certain aspects of the present disclosure.

In contrast to the scintillator/camera systems described above for a C-arm type radiation delivery system, the present disclosure contemplates alternative embodiments for implementation with radiation delivery systems having a bore, for example, a radiation delivery system combined with an imaging system such as an MRI. FIG. 6 shows a simplified example of such a system 600 that includes first and second magnet housings 602 and 604 separated by gap region 612. A radiation source 606 can be mounted to a gantry adjacent to or in a gap region 612. A patient can be positioned on couch 614 inside bore 616 of the magnet so that the gantry can cause rotation of radiation source 606 around the patient.

Figure 7:
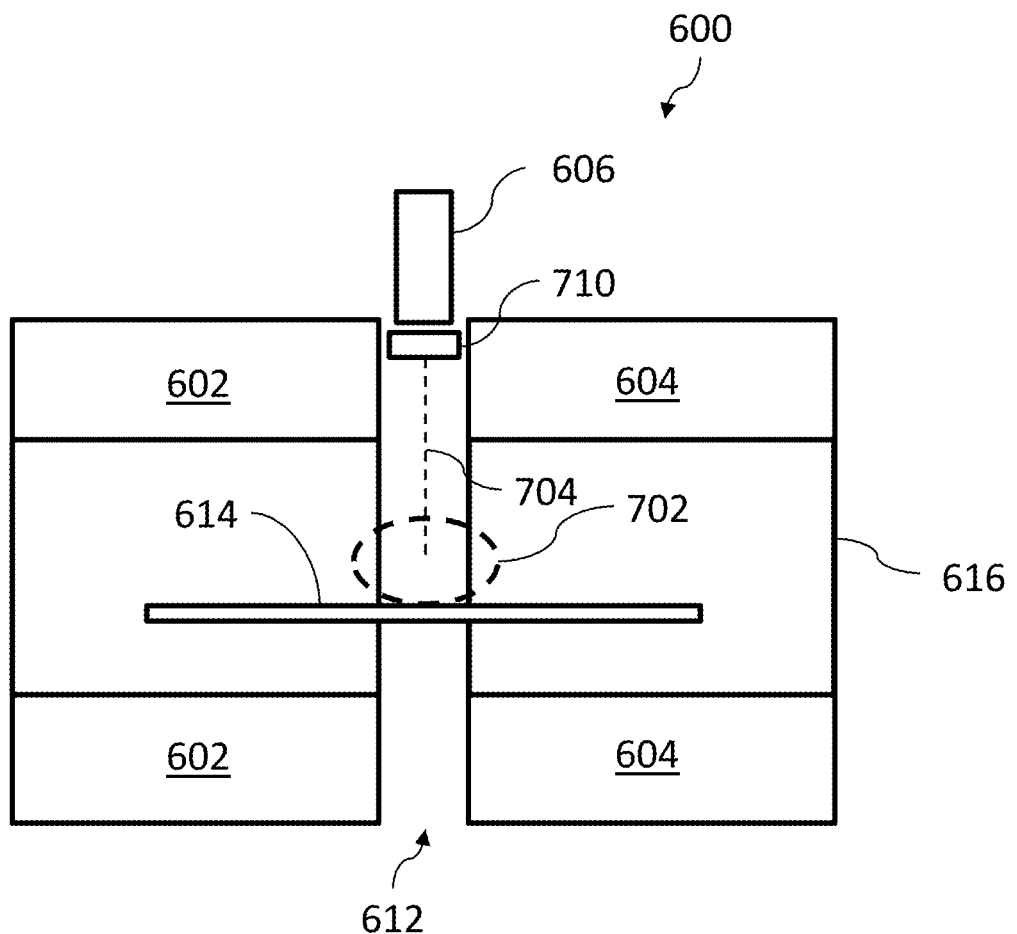
FIG. 7 is a diagram illustrating a side-sectional view of the simplified exemplary combined radiotherapy and medical imaging system of FIG. 6 in accordance with certain aspects of the present disclosure.

FIG. 7 depicts a cross-sectional view of the exemplary system shown in FIG. 6. Such a system can be used to image a target region 702 (e.g., a volume and/or area within a patient), while radiation source 606 emits radiation 704 for patient treatment. Also shown is a multileaf collimator 710 for shaping the radiation beam directed toward the patient. The system illustrated in FIGS. 6 and 7 is only one example of a radiotherapy system having a bore that is compatible with embodiments of the present disclosure. Implementations of the technologies herein may also be used with other types of radiotherapy systems that include a patient bore.

Scintillators that are shaped or configured for radiotherapy systems having a bore may be utilized in certain implementations. For example, as shown FIG. 8, scintillator 810 can be mounted to radiation delivery system 600 such that scintillator 810 substantially follows the contour of a bore 616 of a radiation delivery system 600. As noted above with regard to FIGS. 6 and 7, the bore may be part of an MRI-guided radiotherapy system. "Substantially following the contour of a bore" is understood to include, for example, following the internal surface of the bore or having generally the same contour as the bore but a slightly larger or smaller diameter, etc.

Figure 8:
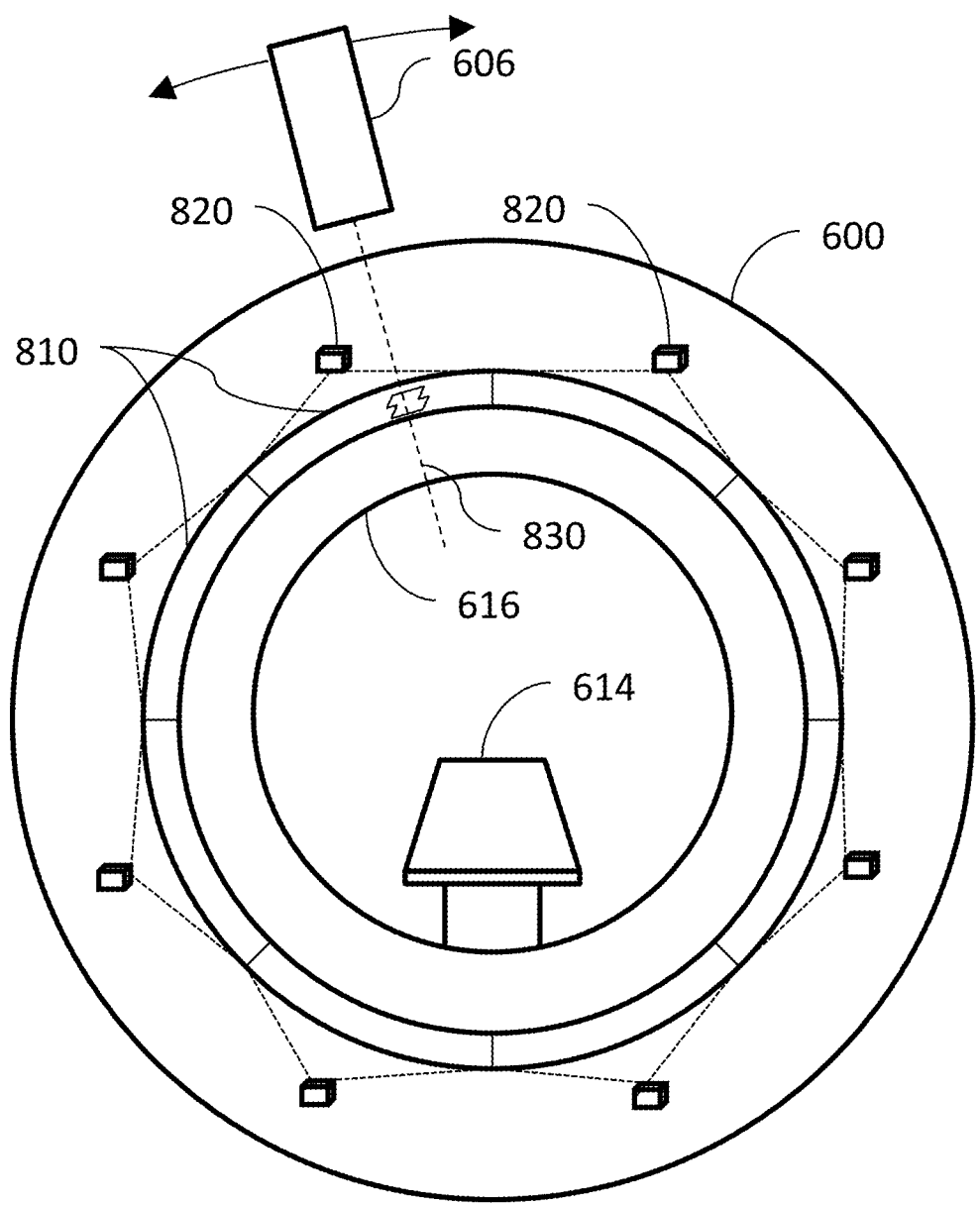
FIG. 8 is a diagram illustrating an end-perspective view down the bore of the simplified exemplary combined radiotherapy and medical imaging system of FIG. 6, showing exemplary scintillators and cameras in accordance with certain aspects of the present disclosure.

The scintillator may be a continuous sheet of scintillating material or may be comprised of multiple sheets. The example of FIG. 8 illustrates an exemplary scintillator having multiple curved sheets of scintillating material, specifically, eight curved sheets, each covering 45 degrees of the bore. In other implementations, the scintillator may be made up of a number of planar sheets of scintillating material. For example, the configuration shown in FIG. 8 could instead be comprised of eight planar sheets, meeting at their edges. It is contemplated that any number of curved or planar sheets can be implemented, in any feasible combination, to cover a desired portion of the bore and they can be located at any radial distance from the axis of the bore.

While the scintillator can extend around the entire circumference of the bore, it is not essential that it do so. For example, the scintillator can cover any degree or angular measure of the bore (e.g., 270 degrees, 180 degrees, 90 degrees, 45 degrees, etc.) and may be constituted of any number of sheets (e.g., ten sheets covering 27 degrees each, 18 sheets covering 10 degrees each, etc.).

As described in further detail herein, mounting the scintillator to the radiation delivery system may include, for example: mounting the scintillator directly to a portion of the radiation delivery system such as the gantry, the linac, the MLC, etc.; mounting the scintillator to the bore of an imaging system associated with the radiation delivery system (e.g., an MRI for an MRI-guided radiation therapy system); and, mounting the scintillator indirectly, for example, mounting the scintillator to a supporting structure that can in turn be mounted to portions of the overall system (e.g., RT device, MRI, etc.).

In some embodiments, the scintillator can be mounted so it is at an angle to the radiation beam or the scintillator can be mounted so that at least one portion of the scintillator remains perpendicular to axis 830 of the radiation beam when the radiation source 606 is controlled to move around the bore. For example, in instances where the radiation beam axis 830 is radial and the scintillator is curved to be concentric with the bore, at least one portion of the scintillator (e.g., where axis 830 intersects the scintillator) would be perpendicular to axis 830.

One or more cameras configured to acquire images of light emitted by the scintillator during delivery of the radiation beam can be utilized. Similar to the previously-described embodiments, these may be mounted so as to have a shallow angle between the scintillator and the camera. For example, the cameras can be configured to be mounted at an angle of greater than 0 and less than 10 degrees relative to the scintillator. In other embodiments, the cameras may be mounted to result in angles of 10-20, 20-30, 30-40, 40-50 or 50-60 degrees between the scintillator and the line of sight of the camera.

Cameras can be placed on the bore at various locations so they are able to view at least a portion of the scintillator. The cameras can be small so as to provide minimal intrusion into the inner volume of the bore where the patient is located. As shown in the example of FIG. 8, each of the scintillator sections or sheets may have a corresponding camera with a field of view covering it (shown approximately by the dotted lines). The number and disposition of the cameras and their fields of view in FIG. 8 are examples only and other configurations are contemplated. For example, the fields of view can cover only a portion of a section rather than an entire section, the cameras can be located at any axial location along the bore, and they can be on either side of the scintillator.

In some embodiments, a support structure can be configured to be mounted to the bore, and the one or more cameras can be fixed to the support structure. In the present example, a support structure configured to be mounted to the bore may include a cylindrical framework that generally conforms to the shape of the bore, such that the supporting structure having the cameras can be inserted or installed in the bore, without the need to mount individual cameras to the bore structure itself. In such embodiments, and other embodiments, such as those described above with reference to FIG. 8, the cameras can be oriented to view respective portions of the scintillator adjacent to the cameras. Here, the scintillator "adjacent the camera" means the scintillator can be located at least partially at the same angular location as the camera. In addition to mounting cameras on such a support structure, other embodiments can include having the scintillator also mounted to the support structure. Such embodiments can allow for the entire assembly of scintillators and cameras to be inserted or mounted to the bore as a unit, rather than as individual components.

In other embodiments, the camera can be mounted to view a portion (i.e., some or all) of a radiation pattern displayed at a computer monitor showing radiation that was delivered to the radiation detector. The camera can be located at any position, for example, attached to the computer monitor via a mounting arm, mounted to a table or wall near the computer monitor, etc. As such, the camera can have any viewing angle relative to the computer monitor.

Accordingly, the disclosure of the present, and parent, applications contemplate, among other things, the general concepts of acquiring images capturing at least a portion of a shape representative of a radiation pattern generated by a radiation delivery system that includes a radiation source configured to deliver a radiation beam.

Thus, in addition to utilizing a scintillator to obtain images, the images can be of a computer monitor of a radiation detector, the operations further comprising determining one or more dimensions of the radiation pattern based on determining a conversion between the images and computer monitor images of the radiation pattern.

As explained further below, the present and parent disclosures thus also contemplate the utilization of the captured images and the calibration techniques described herein during treatment or as part of quality assurance, to perform, for example, dose calculation, collimator position determination (e.g., MLC leaf position), fluence determinations, etc. The captured images can be acquired from the camera aimed at a computer monitor displaying the shape that is representative of the radiation pattern. The camera may be mounted in a fixed relationship to the computer monitor by mounting to the computer monitor itself or another location nearby. To allow for a user to be in front of the monitor, it is contemplated that in some implementations the images can be acquired at an angle not perpendicular to the computer monitor. In some implementations, the camera can be fixed to the computer monitor so that the camera will be at an angle of between 1 and 10 degrees relative to a screen of the computer monitor (with 90 degrees being perpendicular to the screen). In other implementations, the camera can be is fixed to the computer monitor so that the camera will be at an angle of between 4 and 8 degrees relative to the screen of the computer monitor. In some implementations to have a more direct viewing of the computer monitor, the camera can be fixed at a location that maximizes the angle between the camera and the screen. For example, the location can be a wall generally opposite the monitor.

Figure 8A:
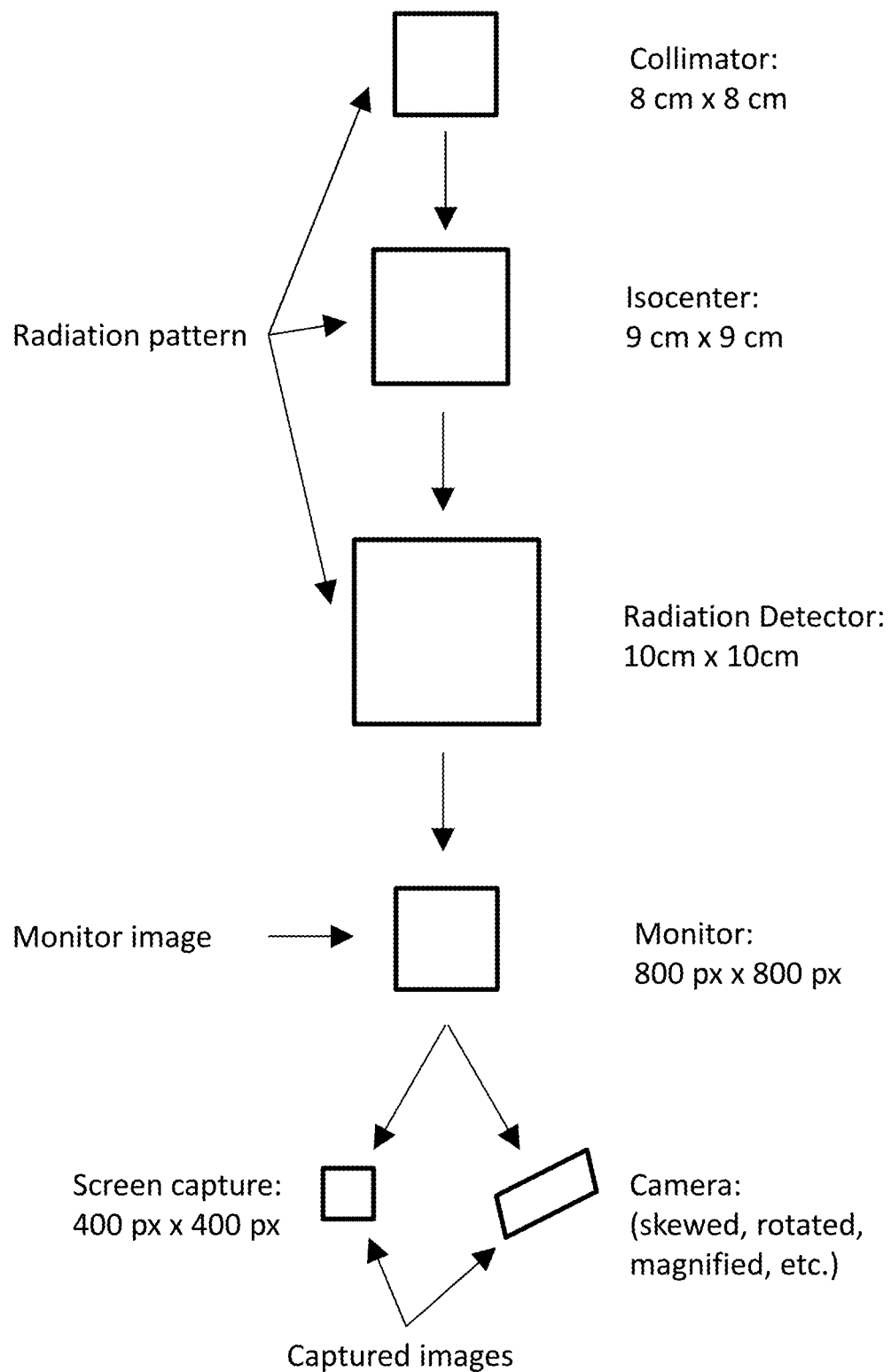
FIG. 8A is a diagram illustrating an exemplary sequence of how radiation patterns and images thereof may appear at different stages of the disclosed systems, in accordance with certain aspects of the present disclosure.

FIG. 8A illustrates an example of how the size of a radiation pattern may vary when captured by a camera viewing a computer monitor (or by screen capture at the computer monitor). The dimensions provided in the example are only for illustrative purposes and are not to scale. For example, a collimator can be controlled to form an aperture of 8 cm×8 cm. Due to beam divergence and based on distances along the beam axis, this aperture can result in a radiation pattern of 9 cm×9 cm at the isocenter and 10 cm×10 cm further along at the radiation detector. The radiation pattern, as displayed at the computer monitor (i.e., the "computer monitor image," could be 800 pixels×800 pixels. If a screen capturing technique is used, the captured images of the radiation pattern could be, for example, 400 pixels×400 pixels. Similarly, if using a camera, due to factors including distance, offset, rotation, viewing angle, etc., the captured images from the camera could be rotated, skewed, magnified, offset, etc. When the images are corrected in software, they can then have the same shape as the radiation pattern (e.g., square), but with their final size in pixels depending on the final transformations used. However, with corrections/conversions, the images can be used to derive dimensions of radiation patterns and/or collimator positions, etc.

The present disclosure provides several methods for determining dimensions of a radiation pattern, positions of a collimator used to shape the radiation field, etc. As described herein, computer monitor images may be captured by a camera or with screen capture software. As previously illustrated in FIG. 8A, a complicating factor can be that the camera (and screen capture software) may generate images having a different resolution. Thus, the present disclosure provides implementations of methods and software algorithms to establish a conversion for the camera or screen capture images to provide a measure of the actual dimensions of the radiation pattern at the radiation detector (or other useful locations). Thus, in general, the software that performs this conversion (also referred to as "image processing module") can determine a conversion between the captured images and the radiation pattern.

In some implementations, the image processing module can receive conversion information entered by a user after measuring the geometric relationship between the camera and the computer monitor. In other implementations, conversion information can be determined based on utilizing imaging of markers placed at known locations. In yet other implementations, conversion information can be determined that establishes a relationship between image intensity and delivered dose.

In other embodiments, the relationship between the pixels size of the displayed image and the radiation detector can be established by the original equipment manufacturer (OEM) a priori. In such circumstances, this calibration process can become a quality assurance process to confirm this relationship is as stated by the OEM.

Information for conversion of camera images received by the image processing module can include: camera angle (which can introduce a different conversion of the horizontal (X) and vertical (Y) pixels in the camera image), distance between the camera and the computer monitor, magnification of the images, offset between the center of the camera's FOV and the center of the viewing field at the computer monitor (i.e., the center of the camera image of the computer monitor not coinciding with the location at the radiation detector of the axis of the radiation beam), the angle of the camera, etc. Other factors that can be considered are the refresh rate of the computer monitor, the frame rate of the camera, either (or both) of which can result in image blurring or missing data. In this way, the operations for determining the conversion can include applying one or more of a scaling, rotation, or skew correction to the images.

Described below are exemplary methods for use with a camera imaging the radiation detector's computer monitor. Then, other exemplary methods are described for directly capturing the output of the computer monitor without the use of a camera.

First, a predefined radiation field can be created that has known dimensions. For example, a collimator can be controlled to have an aperture 8 cm×8 cm. The camera can then acquire images of the resultant radiation pattern at a scintillator or from the computer monitor. In software, the conversion between pixels in the camera image and the known size of the aperture can be established as a calibration for the camera images. Thus, when imaging a radiation field of unknown or varying dimensions, this calibration can be applied to convert the camera images into actual dimensions of the aperture. Similarly, with a known beam divergence and distance from the collimator to the radiation detector, isocenter, or any other location, the images can then be converted or used to measure the radiation field at those locations as well.

In another implementation, a graticule or other structure having markers representing known distance(s) and/or having known thicknesses can be placed at any location (e.g., on the radiation detector, at the isocenter, on the scintillator, etc.) and imaged. The markers can attenuate the beam and aid in determining image calibrations, as described further below.

In some implementations, acquiring of images can be performed by screen capture of the computer monitor displaying the shape representative of the radiation pattern. Such implementations have advantages in that additional hardware (e.g., a camera) is not required, which eliminates error that could be introduced by uncertainty in a camera angle or position. Described below are some factors that can be implemented in determining conversions utilizing images acquired through screen capture.

In one implementation, the conversion can be based on a ratio of pixels in the computer monitor images to the pixels in the acquired images. In another implementation, calibration methods similar to those discussed above can be performed where a radiation pattern of known dimension is projected onto the radiation detector. With known dimensions of the radiation pattern in pixels in the captured images, a conversion factor can be established. Thus, determining the conversion can include applying a scaling (likely) or rotation (if applicable). The scaling or rotation can utilize information entered by a user.

In some implementations, the acquiring of images can be performed through utilization of video capture techniques applied to video outputs of the radiation detector. The term radiation detector in this case refers not only to the detector itself (e.g., an EPID panel) but also to its associated electronics, which may include a computer console, a monitor, etc., that are used in conjunction with an EPID panel to process and display the radiation patterns detected by the EPID.

Some radiation detectors can generate output in the form of "digital video signal output." As used herein, the term "digital video signal output" and other forms of the term encompass output from the radiation detector (e.g., a video of the measured radiation pattern) that can be displayed at a dedicated monitor of the radiation detector or electronically transmitted over a connection for, e.g., storage or display at a remote system/monitor. The digital video signal output can be provided from the radiation detector via a variety of physical connections. For example, the digital video signal output may come from an HDMI port, an ethernet or RJ45 connector, etc. The formatting of the digital video signal output can determine how it may be used and if further processing is needed.

Similar to other implementations described herein, the images acquired from the digital video signal output (e.g., acquired during or after delivery of a radiation beam) can capture (e.g., represent/contain) at least a portion of a shape representative of a radiation pattern generated by a radiation delivery system that includes a radiation source configured to deliver the radiation beam.

Figure 9:
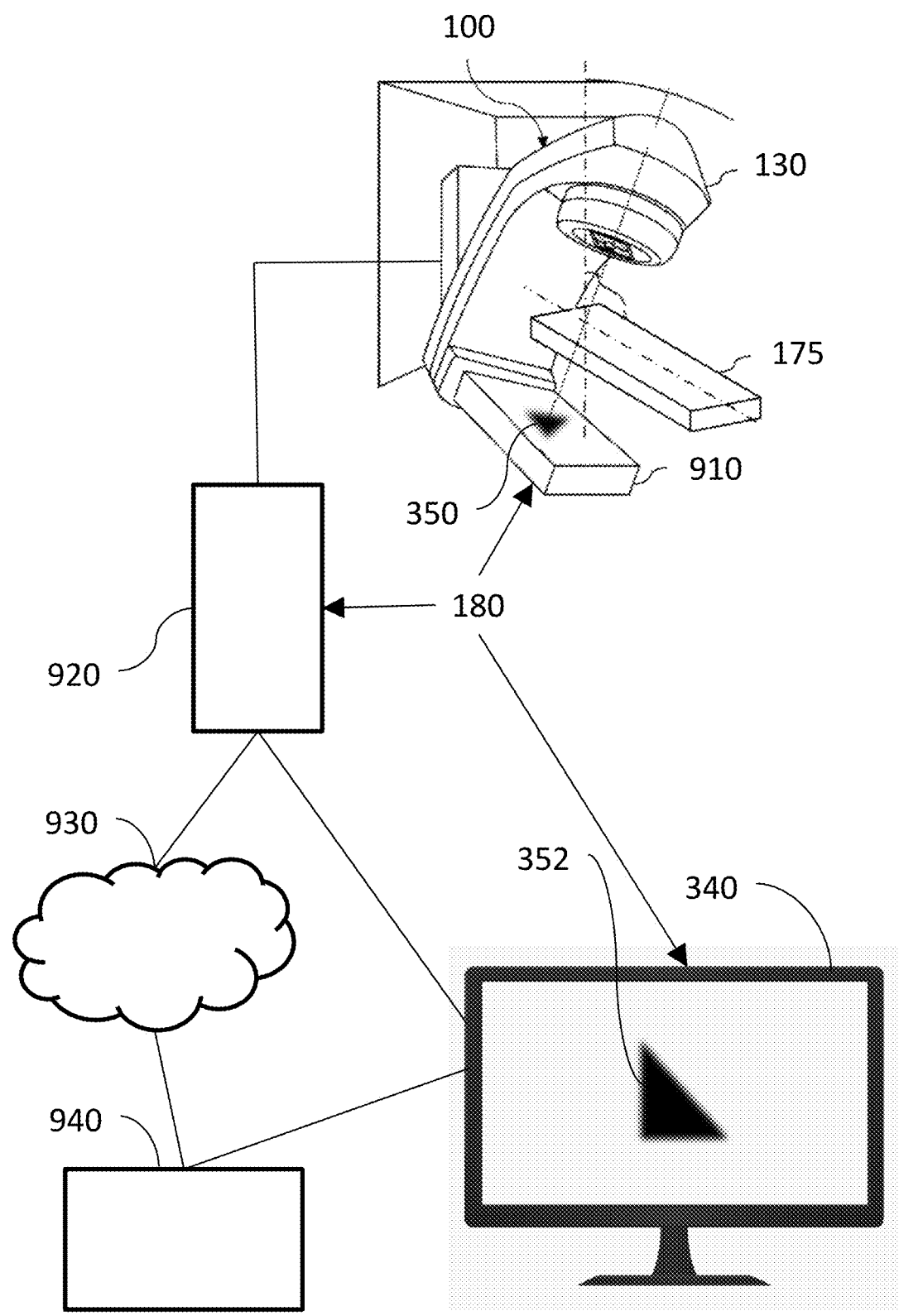
FIG. 9 is a diagram illustrating an exemplary system including a radiation detector in communication with a server for radiation delivery QA in accordance with certain aspects of the present disclosure.

As used herein, a radiation detector may be any sort consistent with the present disclosure (e.g., any configured to measure a radiation pattern). One example of a radiation detector 180 can include an EPID as shown in FIGS. 3A and 9. FIG. 9 depicts an implementation where radiation detector 180 can include EPID panel 910 for receiving the radiation, console 920 that processes data from the EPID panel, and monitor 340 for displaying the shape 352 of radiation pattern 350. In general, panel 910 can refer to any radiation-sensitive portion of a radiation detector, console 920 can refer to any computing systems associated with processing data from panel 910 and monitor 340 can refer to any display device for showing data associated with the radiation detector.

Another example of a radiation detector may be a scintillator coupled to an array of photomultiplier tubes or a scintillator imaged with a camera. Output of the array or the camera can be digitized to also be digital video signal output, similar to the EPID radiation detector example. Accordingly, no specific type of radiation detector (e.g., an EPID) is required or essential for use with the image/video capture concepts disclosed herein.

Some implementations of radiation detector 180 can include console 920 producing a digital video signal output formatted for display on monitor 340. The digital video signal output can than later be provided as a video stream to a Quality Assurance (QA) server 940. Other implementations can, additionally or alternatively, provide a video stream at QA server 940 that is received over network 930 without being relayed through monitor 340. The acquisition of images useful for radiation therapy QA can also include extracting images from a video stream received at QA server 940. As used herein, the term "video stream" encompasses data formatted such that it can be transmitted/received over a network connection. Examples of formats for a video stream can include, for example, H.264, H.265, RTMP, RTSP, UDP, HTTP, M3U8, or Multicast SRT.

Figure 10:
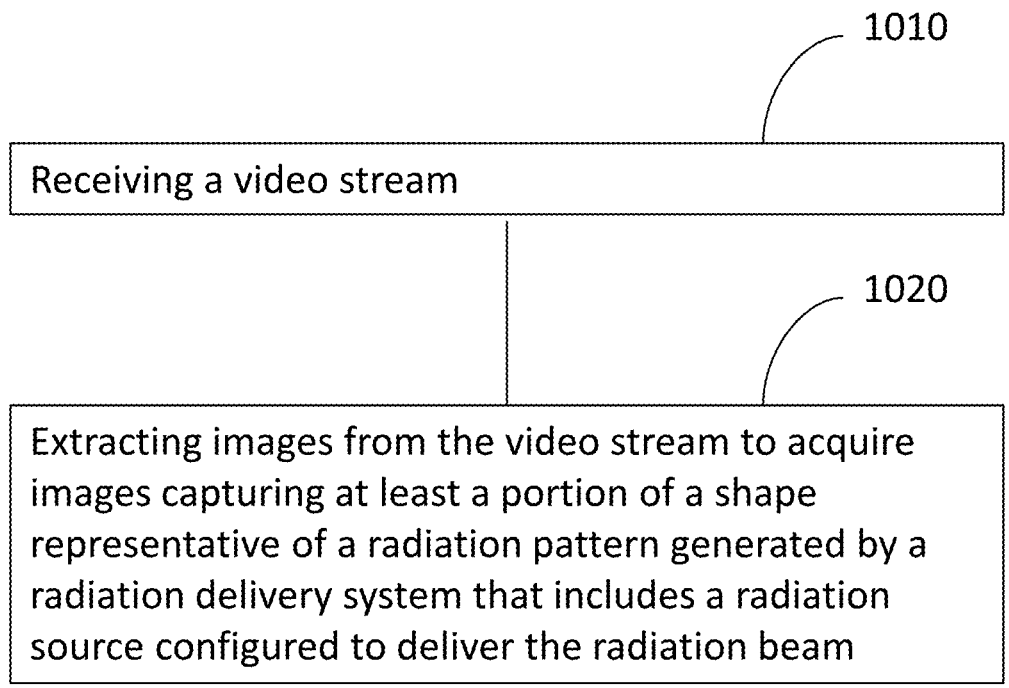
FIG. 10 is a diagram illustrating an exemplary method of extracting images from a video stream in accordance with certain aspects of the present disclosure.

As illustrated by the flow chart in FIG. 10, computer software can perform operations to acquire images for QA by extracting them from a video stream. In the exemplary implementation of FIG. 10, at 1010, a video stream can be received. The receipt of the video stream can be at, for example, QA server 940 but may also be at any other associated computing systems that may perform preprocessing or other operations on the video stream before delivery to the QA server. For example, the video stream may go through routers, encryption/decryption hardware, etc., before arrival at the QA server.

At 1020, images can be extracted from the video stream in several different ways to acquire images capturing at least a portion of a shape representative of a radiation pattern generated by a radiation delivery system that includes a radiation source and beam limiting devices configured to deliver and shape the radiation beam. Image extraction can be performed, for example, by isolating individual video frames from the video stream and saving the video frames as image files. In another implementation, digital interpolation can be used to generate frames at time indices between those of the closest frames (such as when the video frame rate is lower than desired). For example, if the video frame rate was 10 frames per second (fps) but 30 frames per second were needed, two intermediate frames can be generated for each frame based on digitally interpolating adjacent frames in the video stream. In another implementation, digital averaging can be used on a comparatively high frame rate video stream. For example, if the video stream corresponded to a frame rate of 120 fps but 30 fps is needed, four frames can be digitally averaged (e.g., averaging pixel intensities) to generate a single frame. Other implementations can include processing such as skipping some frames, e.g., to sparsely sample the video stream, digitally averaging overlapping groups of frames, or otherwise smoothing the video stream, removing artifacts resulting from video capture, or calculating differences between frames or images from different moments in time. For example, some radiation detectors acquire and accumulate image data over a given acquisition period and thus any given frame is actually an accumulation of image data. In such cases, earlier frames may be subtracted from later frames.

Figure 11:
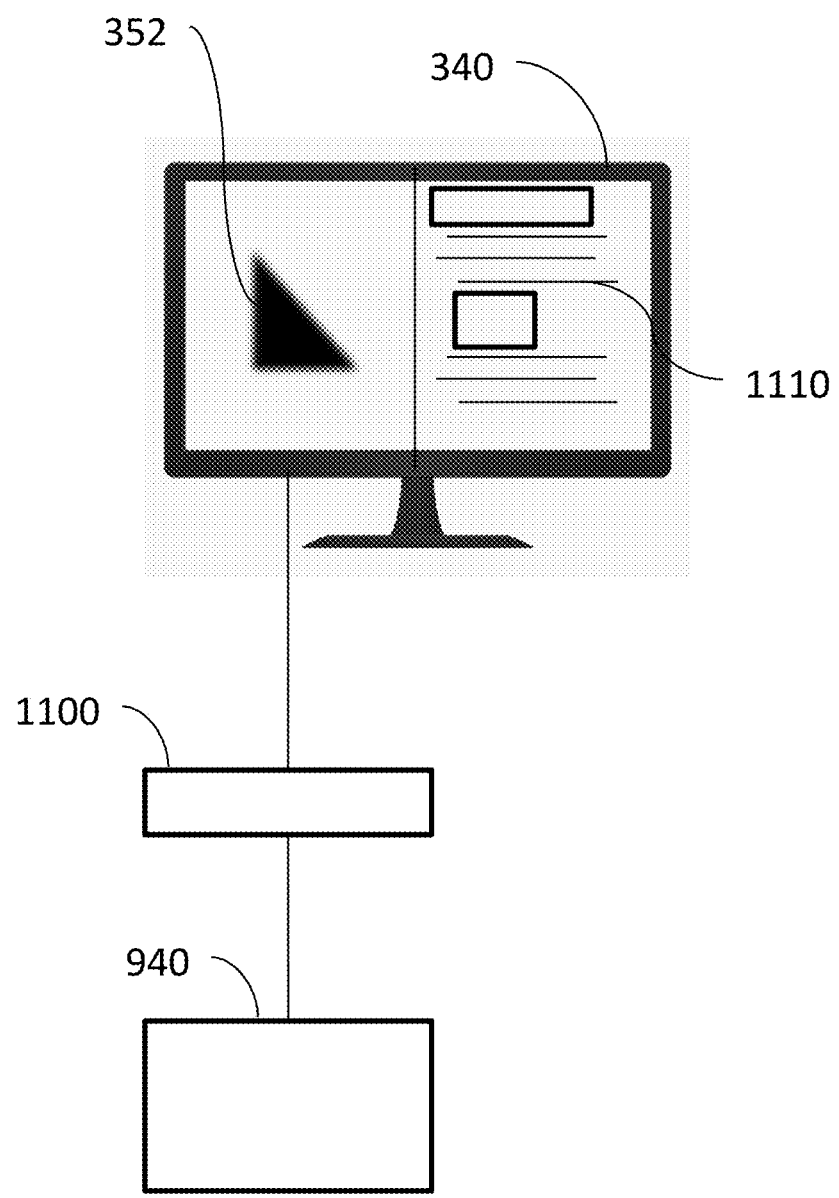
FIG. 11 is a diagram illustrating an exemplary system including a monitor used with a radiation detector providing a digital video signal that is output to a video encoder in accordance with certain aspects of the present disclosure.

FIG. 11 illustrates utilizing a video encoder as part of the video capture process. In this implementation, a digital video signal output can be provided to a video encoder 1100 by monitor 340 that is associated with the radiation detector. The monitor can do so via an HDMI port, DVI port, etc. In the example of FIG. 11, the monitor depicts the display of shape 352 of the radiation pattern on the left half of the screen and additional information 1110 (e.g., patient name, ID, or other data) on the right half of the screen. As used herein, when monitor 340 is said to be "associated with" the radiation detector, this means that the monitor is specifically provided for displaying output from the radiation detector. For example, the monitor may be a screen integrated into the radiation detector or a dedicated peripheral that comes with the console and panel. Alternatively, the monitor may be any sort of monitor that has been integrated with the radiation detector for the display of information.

Video encoder 1100 can receive the digital video signal output from the monitor at an input port (e.g., HDMI, DVI, etc.). The video encoder can then convert/encode the digital video signal output into a video stream. The video stream can then be output from the video encoder via a LAN connection or other connection such that it may be streamed to computing systems for performing radiation therapy QA (e.g., QA server 940). In this way, the converting (or encoding) can take the digital video signal output, which can initially be in a format suitable only for direct video display at a monitor and encode it into a format suitable for transmission over network connections. The converted or encoded digital video signal output is then considered to be a "video stream." Video stream formats can include, for example, MPEG, WebM, AVI, MOV, Flash Video, etc.

Figure 12:
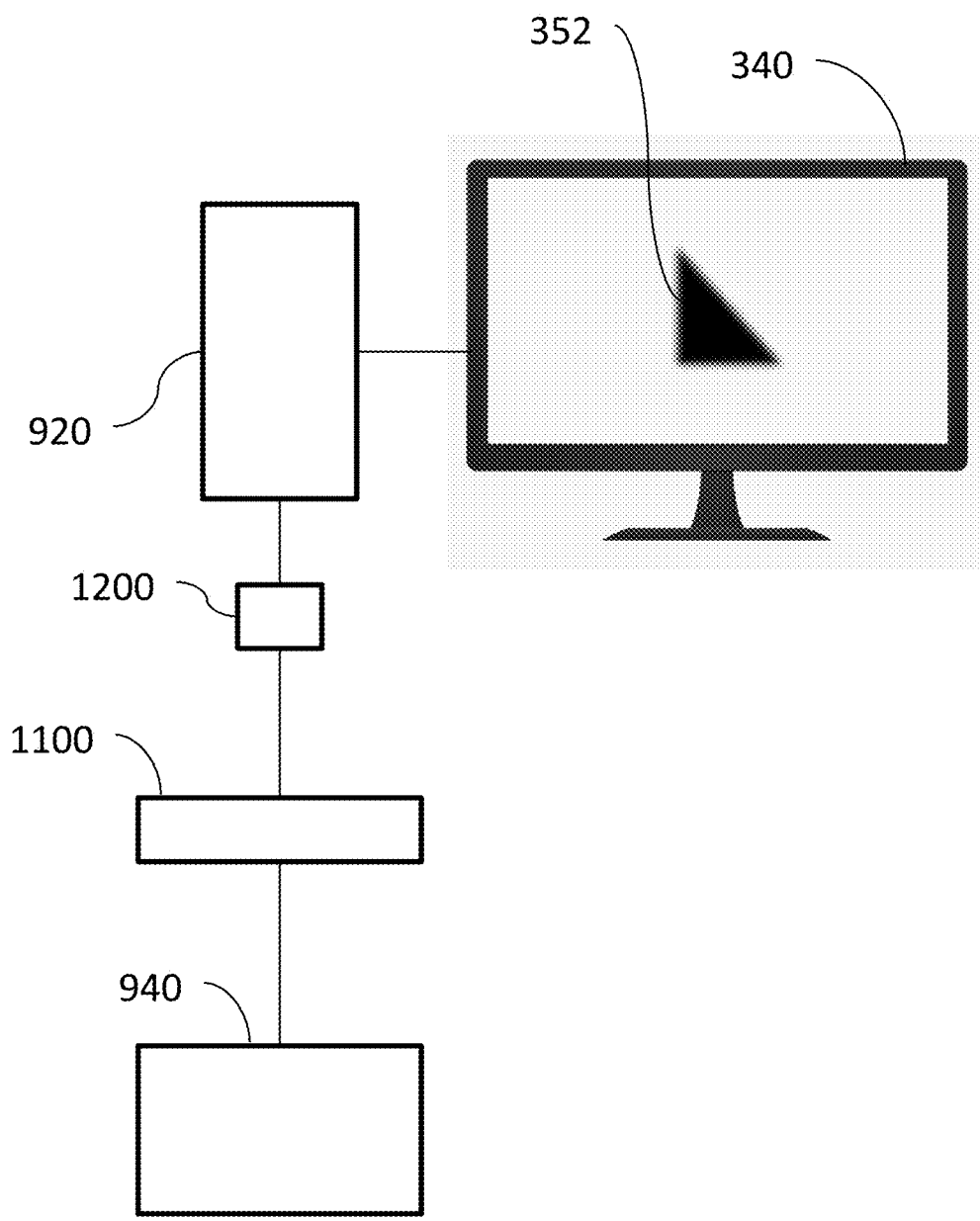
FIG. 12 is a diagram illustrating an exemplary system including a console of a radiation detector providing a digital video signal output to a video encoder in accordance with certain aspects of the present disclosure.

FIG. 12 illustrates a video encoder receiving a digital video signal output from a radiation detector. In general, rather than requiring that the digital video signal output be received specifically from a monitor, the digital video signal output can be received at the video encoder from any component of the radiation detector. For example, the digital video signal output can be received from the console of the radiation detector. As used herein, the term "console" generally refers to computers or other hardware associated with the radiation detector but generally excluding the panel and the monitor. The console can provide the digital video signal output via, for example, an ethernet or RJ45 connector, an HDMI port, etc. In some implementations, a physical converter 1200 can be utilized to convert an ethernet or RJ45 connector to an HDMI port or other connectors such as VGA, DVI, DisplayPort, etc., which can then be connected to the video encoder via a corresponding type of cable. However, the use of such a converter 1200 is not essential. For example, in other implementations such as ones where video encoder 1100 may already have an ethernet or RJ45 connector, the connection between console and the video encoder can be made directly without the use of a converter. Once the digital video signal output is received by the video encoder, the video encoder can convert the digital video signal output to the video stream, as described herein. The video stream can then be streamed to QA server 940 or another connected system.

Figure 13:
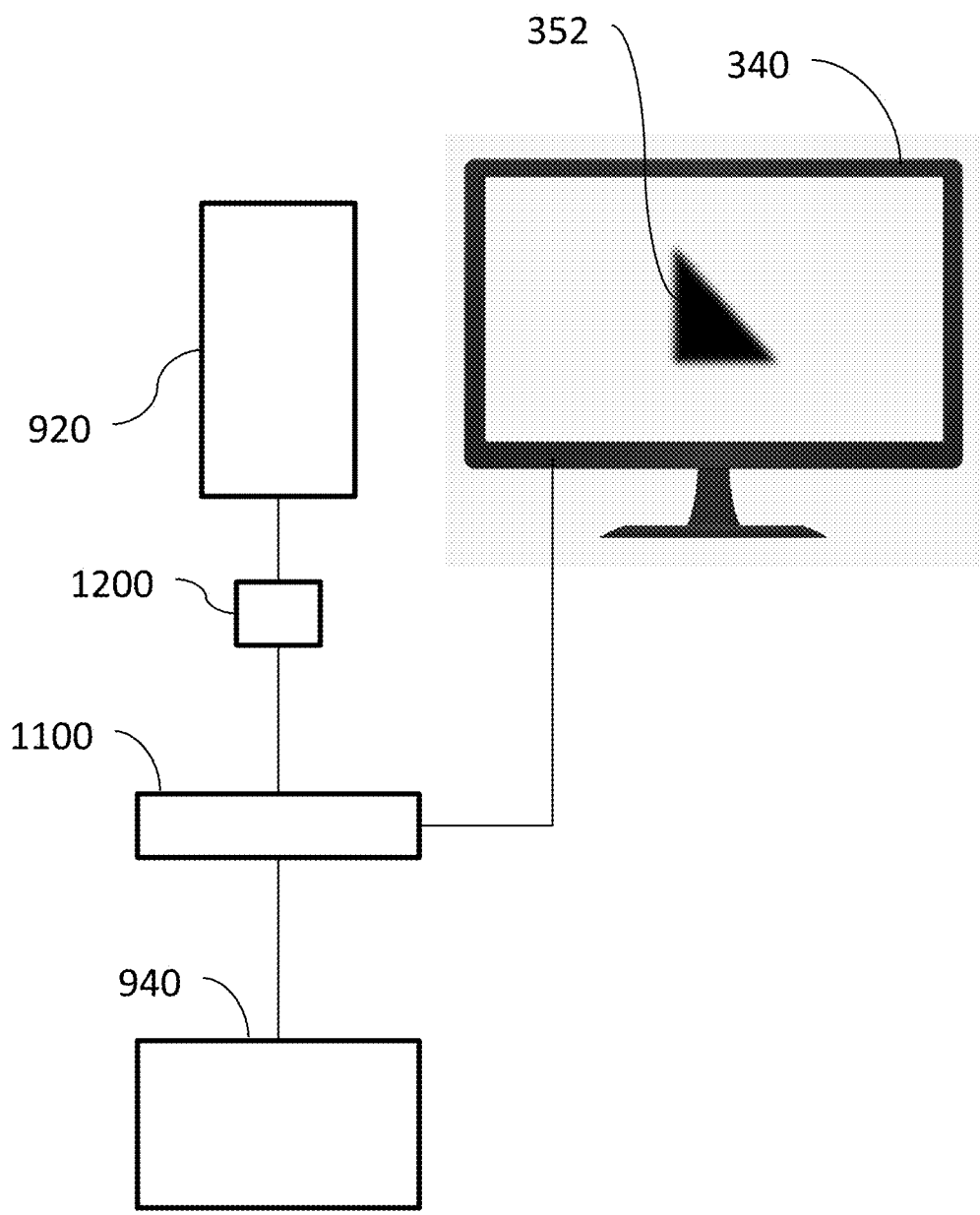
FIG. 13 is a diagram illustrating an exemplary system including a video encoder providing a video stream to a QA server and providing digital video signal output to a monitor in accordance with certain aspects of the present disclosure.

FIG. 13 illustrates a video encoder 1100 additionally sending a digital video signal output to a monitor 340. In implementations where the monitor is part of a radiation detector, the disclosed system can be configured to transmit the digital video signal output from the video encoder to a monitor associated with the radiation detector. For example, the video encoder can have an HDMI output port that can be connected to a monitor with an HDMI input port. Such implementations may be utilized to provide uninterrupted video display of information from the radiation detector.

Figure 14:
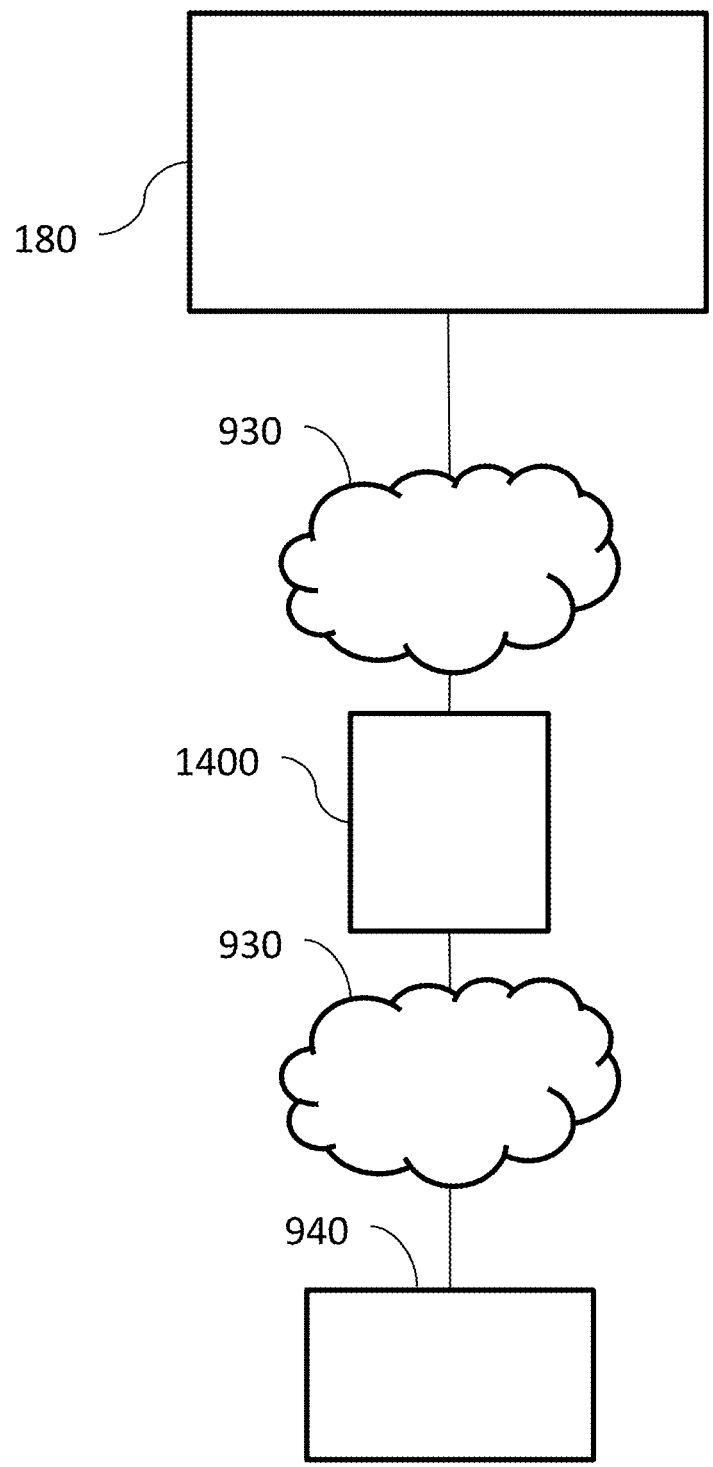
FIG. 14 is a diagram illustrating an exemplary system including a server, which is not part of a radiation detector, providing a video stream to a QA server in accordance with certain aspects of the present disclosure.

FIG. 14 illustrates an example of a QA server 940 receiving a video stream from a server 1400 that is not part of the radiation detector 180. In some implementations, the video stream can be received from a server 1400 that is not part of the radiation detector. When referring to a server "that is not part of" the radiation detector, this means that server 1400 would not include processors in panel 910, console 920, or monitor 340. One example of server 1400 is a remote computing system, connected to network(s) 930, for relaying a video stream version of the digital video signal output. The remote computing system can be, for example, part of a hospital's computing system that provides video from the radiation detector to physicians. In some implementations, the digital video stream can be displayed live/in real-time such as radiation is detected and imaged by the radiation detector.

For QA server 940 to receive the video stream, one implementation can include QA server 940 connecting to server 1400 via a website link or URL. The QA server can then download the video stream from server 1400. Processing of the video stream into video files and/or images useful for radiation therapy QA can then proceed as described herein.

In another implementation, the system can obtain a recorded video stream from the video stream obtained from server 1400. For example, while the previous implementation contemplated that such streaming may be "live" or "real-time," other implementations can utilize a recording of a previously acquired video stream such that the acquired images utilized for radiation therapy QA can be obtained from the recorded video stream. In some implementations, the recorded video stream can be accessed from a video archive. Such an archive can include ones organized, for example, by patient, timestamp, or other identifier. In implementations where the recorded video stream is in the format of video files or images that can be used without the encoding needed for a video stream, such a recorded video stream can be directly usable by QA server 940.

In some implementations, for example, where the use of a video encoder is not needed due to the radiation detector providing a usable video stream, a recorded video stream can be generated from a video stream originating from the radiation detector. In this way, the acquired images used for radiation therapy QA can be obtained from the recorded video stream, rather than requiring a video encoder or real-time analysis.

In other implementations, start and end points of the recorded video stream can be determined by analyzing the video stream to determine when the patient changes. For example, individual patients may be identified in the video stream by a patient name or identification number. QA server 940 can analyze the video stream to identify the patient (e.g., determining/analyzing portions of video frames in locations where the name is displayed) and isolate and/or extract one or more frames or video segments from the entire received video stream for use in QA analysis. Other identifying information can also be utilized, for example, timestamps that are known to be associated with a patient. In yet other implementations, rather than restricting a segment of a video stream broadly to a patient, a similar process can be implemented (e.g., based on a treatment fraction or timestamp) to obtain start and end times corresponding to a particular portion of the treatment delivery for the patient. For example, start and end times for treatment of a tumor at a given gantry angle may be obtained, intermediate video stream data may then be ignored until another start time is determined, and then the start and end times for treatment of the tumor at a different gantry angle can be obtained. Similar methods can be used outside patient treatment, such as during commissioning or calibration where radiation may be delivered to a phantom as part of radiation delivery QA.

Based on the present disclosure relating to use of cameras, screen capture software, and video stream capture hardware/software to obtain images of and calculate dimensions associated with a radiation pattern, the following example of use is provided. One such method can include the following steps (though not limited to the order shown below):

Step 1—placing a graticule with markers that have known thicknesses and/or known dimensions between the markers. The markers can be made of one material or of different materials of similar or varying radiation attenuation. In this way, the markers will be visible in images due to being opaque to delivered radiation.

Step 2—initiating delivery of a radiation beam.

Step 3—imaging the graticule with the radiation detector (e.g., an EPID) during delivery of the radiation beam.

Step 4—acquiring images during the delivery of the radiation beam, the images capturing at least a portion of the graticule (e.g., from screen capture, a computer monitor with a camera aimed at it, or video stream capture).

Step 5—determining a conversion factor based on at least the known dimensions of the graticule and the acquired images.

In some embodiments, the shapes of the radiation pattern (e.g., EPID images) may be displayed on the screen along with additional information 1110. One example of this is shown in FIG. 11, depicting an exemplary shape 352 on the left half of the screen. Thus, in embodiments where the video capture is performed by screen capture, video camera, HDMI out of a monitor, etc., it is understood that additional processing steps may be required in order to identify the location "on the screen" of the EPID image.

As shown in the example of FIG. 11, the software controlling the display of the images may cause the pane with shape 352 to not occupy the full screen. For example, the software may have a preset display configuration or allow for resizing the pane. Accordingly, some implementations can include auto-detecting elements of interest, such as the location of the borders of the pane containing the shape, locating other visual markers in the image display such as the patient name and ID, etc. Auto-detection can be performed by direct reading if such display data is available in a data file or embedded in the video stream. In embodiments where such display data is not available, image analysis tools such as edge or object detection (e.g., of displayed border lines or text) can be utilized to determine the locations of the borders or selected visual markers. In this way, the additional information 1110 may be disregarded and the boundaries of the area containing shape 352 can be accurately determined. Similarly, determining a patient name/ID can be performed no matter where they are presented on the display.

Methods and software that enable the determination of MLC leaf positions are disclosed herein. Leaf positions can be reflected in scintillator radiation patterns imaged by one or more cameras, obtained via screen capture software, or obtained via video stream capture hardware/software, as described above. In one embodiment, leaf position determination can be facilitated by analyzing the edges of radiation patterns. As used herein, "radiation pattern" means the image of (or data representing the image of) a) scintillator light emitted due to interaction between the scintillator and a radiation beam and/or b) electronic data representing radiation as measured by a radiation detector.

Figure 15:
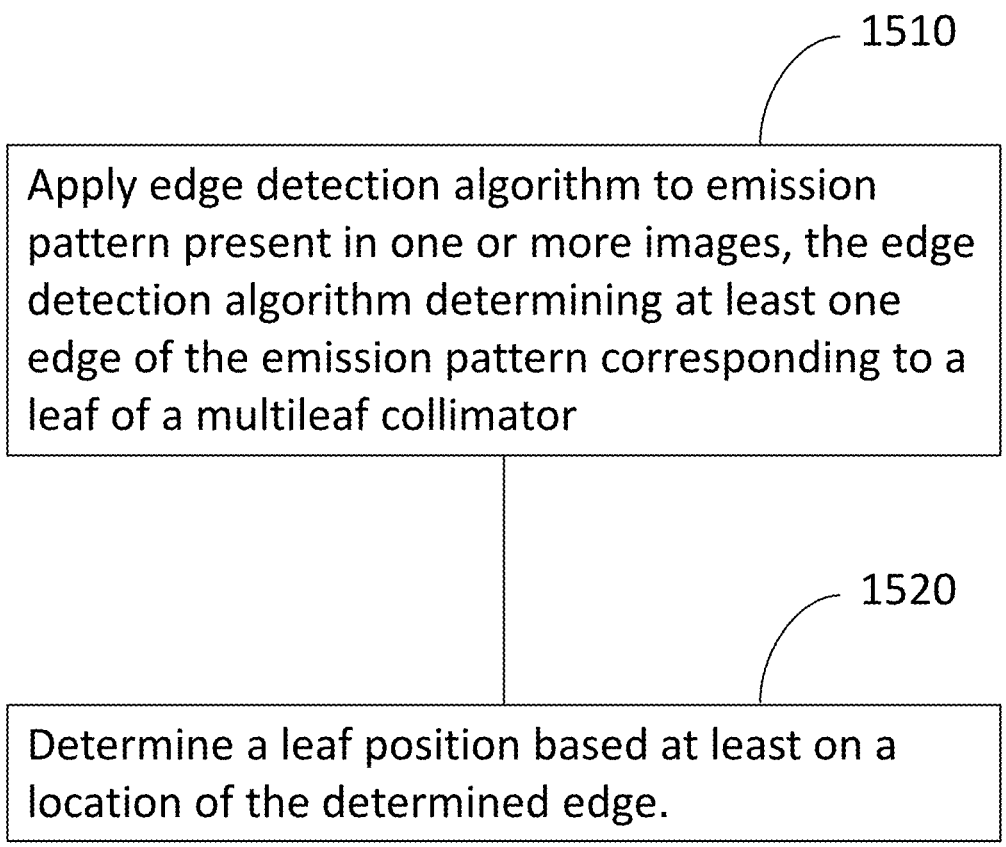
FIG. 15 is a diagram illustrating an exemplary method of determining leaf positions of a multileaf collimator in accordance with certain aspects of the present disclosure.

As illustrated by the example in FIG. 15, computer software (e.g., executed at QA server 940) can perform operations to determine edges of a radiation pattern. For example, at 1510, using the image data acquired from the camera(s) and/or video stream(s), an edge detection algorithm (e.g., a Canny edge detection algorithm) can be applied to a radiation pattern present in the images. The edge detection algorithm can determine at least one edge of the radiation pattern corresponding to a leaf of a multi-leaf collimator. From this, at 1520, a leaf position can be determined based at least on a location of the determined edge. Following this determination, it is possible to compare leaf positions during delivery of the radiation beam with planned leaf positions (e.g., as dictated by a radiation therapy plan and/or detailed in system log files). The comparison can thus be utilized in radiation therapy quality assurance.

The process of determining leaf positions can then include, for example, compensating for image distortion caused by (or inherently present in) a given camera or camera system. For example, lens aberrations, and camera placement with respect to the scintillator can be accounted for. One method of accounting for optical effects from the camera system can include performing a calibration procedure with a well-known pattern that allows for a mapping of points in the image acquired by the camera to real positions in the object plane (e.g., the plane of a planar scintillator sheet). This correction/mapping can be performed for any number of opposing leaves of the MLC.

As part of radiation therapy quality assurance, it can be desired to determine leaf positions at a plane through the isocenter. One method for doing so can include determining the effective size of an opening between collimator leaves at a plane parallel to the isocenter plane. Then, the effective MLC leaf positions at the isocenter plane can be determined based on the effective size, when geometrically extended to the isocenter plane.

Figure 16:
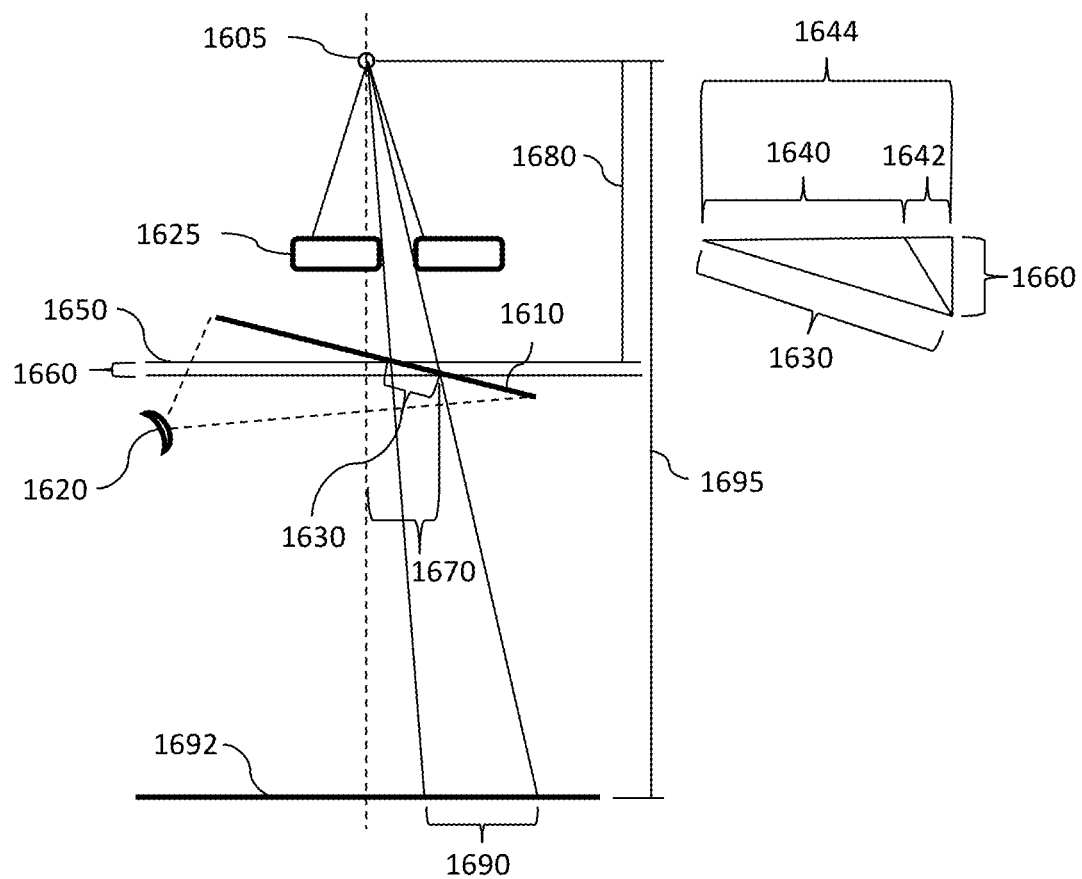
FIG. 16 is a diagram illustrating an exemplary geometric method of determining a leaf position of a multileaf collimator from a radiation pattern in accordance with certain aspects of the present disclosure.

An exemplary arrangement of a simplified system used for the above determination is illustrated in FIG. 16. Here, an example of a tilted scintillator 1610 is shown with a camera 1620 imaging the scintillator 1610. The radiation from radiation source 1605 passing through the MLC 1625 results in a radiation pattern at the scintillator. The shape of the radiation pattern is a length (length$_{screen}$) 1630 that corresponds to the size of the opening between MLC leaves (which can be directly related to the position of the MLC leaves). One exemplary formula for determining the length (length$_{pp}$) 1640 at on a plane parallel 1650 to the isocenter plane 1692 can be expressed as shown in Eq. 1, below.

$$\text{length}_{pp} = \sqrt{\text{length}_{screen}^2 - \text{height}^2} + \text{height} \frac{x}{(d_1 + \text{height})}. \quad (1)$$

In Eq. 1, the height is the height 1660 of the radiation pattern as measured in the vertical direction (or parallel to the beam axis). X is the X-coordinate 1670 of the right edge of the radiation pattern. d1 (element 1680) is the height from the radiation source to the plane parallel to the isocenter plane. The expanded view on the right side of FIG. 16 illustrates that length$_{pp}$ 1640 can be found by accounting for the vertical projection 1642 of the radiation pattern to the plane parallel 1650. Once length$_{pp}$ is found the length (length$_{iso}$) 1690 at the isocenter plane 1692 can be determined according to the following relation:

$$\text{length}_{iso} = \frac{d_3}{d_1} \text{length}_{pp}. \quad (2)$$

In Eq. 2, d$_2$ (element 1695) is the distance from the radiation source to the isocenter plane 1692. The above description and solution of the simplified geometrical arrangement of the scintillator and camera system should not be considered limiting or exclusive of other solutions that may be implemented for embodiments described herein. Furthermore, it is readily apparent that the above disclosure for a flat scintillator can apply to any flat surface or its equivalent, for example, the above-described computer monitor or image files obtained via screen capture of the computer monitor.

The methods and operations described herein can further enable the determination of fluence maps at the isocenter plane, which can be useful for performing radiation therapy quality assurance. For example, the present disclosure contemplates software that can perform operations that include calculating a fluence map based at least on the leaf positions determined using the scintillator and also on beam output data obtained from the radiation therapy system. Furthermore, operations such as calculating a dose at a target location based at least on the fluence map and a patient image obtained from an imaging system may also be performed. Fluence maps, dose calculations, collimator shapes/MLC leaf positions, and other quantities that can be derived with the benefit of the disclosure herein are also described in commonly owned patent applications: U.S. patent application Ser. No. 14/694,865 (now U.S. Pat. No. 10,617,891) "Radiation detector Calibration" and U.S. patent application Ser. No. 15/395,852 "Determination Of Radiation Collimator Component Position," the disclosures of which are incorporated by reference in their entirety.

Below is one example of a method of calibrating the disclosed radiation detector monitoring system to allow accurate determination of delivered dose at the radiation detector. This example allows the user to establish a relationship between the dose delivered by the RT system and the intensity of the pixels as seen on the monitor and the image acquired by the radiation detector. The exemplary method can include any or all of the following steps, not all of which need be performed in the order shown.

Step 1—The user can deliver a series of fixed (e.g., square or rectangular) radiation patterns, each pattern at a different dose level.

Step 2—For each radiation pattern, the user can enable recording of the monitor screen by the camera or screen capturing via the software interface to the radiation detector system.

Step 3—The user can turn the beam off and stop the camera or screen capturing software.

Step 4—The camera or screen capturing software can write out a file containing a video of the screen during image acquisition.

Step 5—The user can open the video file and measure the pixel intensity via software. This can be a statistical measure such as the average or median intensity in an area of the radiation pattern.

Step 6—The user can enter the dose level for that radiation pattern thus establishing a relationship between the pixel intensity and the delivered dose from the radiation therapy system.

Step 7—The user can repeat this process for all fields referred to in Step 1.

Step 8—The dose calibration can then be saved for use during treatment or later quality assurance. In some implementations, the method may be used in conjunction with the processes described in U.S. patent application Ser. No. 14/694,865 (now U.S. Pat. No. 10,617,891) and U.S. patent application Ser. No. 15/395,852.

A further example of use is provided, describing a clinical treatment workflow. The exemplary method can include any or all of the following steps, not all of which need be performed in the order shown.

Step 1—The user can set the patient up for treatment and ready the radiotherapy delivery system for treatment.

Step 2—The user can manually start video acquisition of the monitor by the camera or screen capturing software. Acquisition may occur continuously, and an image processing module (i.e., a collection of software operations and processors utilized for image processing, such as QA server 940) automatically processes the captured video files into segments in which the beam was being delivered at various points in the treatment.

Step 3—The user can initiate beam delivery and the RT delivery system can deliver all treatment beams to the patient.

Step 4—Treatment ends and the user can stop video acquisition of the monitor by the camera or screen capturing software.

Step 5—The camera or screen capturing software can write out a file containing a video of the monitor during image acquisition.

Step 6—The image processing system can automatically process the video file. This can be achieved by a software routine that monitors the folder in which the video files are saved.

Step 6a—Alternately, the user can manually transfer the video file to a predefined location or opens the video file directly in the image processing system.

Step 7—The image processing system inputs the video file into a software module (e.g., an image processing module) containing the algorithm as defined herein or by either of U.S. patent application Ser. No. 14/694,865 (now U.S. Pat. No. 10,617,891) and U.S. patent application Ser. No. 15/395,852. The software module can compute the leaf positions as function of time. This information can be used to generate a DICOM RT Plan object that can be used for dose computation.

In the following, further features, characteristics, and exemplary technical solutions of the present disclosure will be described in terms of items that may be optionally claimed in any combination:

Item 1: A computer program product comprising a non-transitory, machine-readable medium storing instructions which, when executed by at least one programmable processor, cause the at least one programmable processor to perform operations comprising: acquiring images capturing at least a portion of a shape representative of a radiation pattern generated by a radiation delivery system that includes a radiation source configured to deliver the radiation beam.

Item 2: The computer program product of Item 1, the operations further comprising receiving a video stream, wherein the acquiring is performed by extracting the images from the video stream.

Item 3: The computer program product of any one of the preceding Items, the operations further comprising receiving, at a video encoder, a digital video signal output from a monitor associated with a radiation detector; and converting, with the video encoder, the digital video signal output to the video stream.

Item 4: The computer program product of any one of the preceding Items, the operations further comprising receiving, at a video encoder, a digital video signal output from a radiation detector; and converting, with the video encoder, the digital video signal output to the video stream.

Item 5: The computer program product of any one of the preceding Items, the operations further comprising transmitting the digital video signal output from the video encoder to a monitor associated with the radiation detector.

Item 6: The computer program product of any one of the preceding Items, wherein the video stream is received from a server that is not part of the radiation detector.

Item 7: The computer program product of any one of the preceding Items, the operations further comprising generating a recorded video stream from the video stream obtained from the server, wherein the acquired images are obtained from the recorded video stream.

Item 8: The computer program product of any one of the preceding Items, the operations further comprising generating a recorded video stream from the received video stream, wherein the acquired images are obtained from the recorded video stream.

Item 9: The computer program product of any one of the preceding Items, the operations further comprising determining start and end points of the recorded video stream by analyzing the video stream to determine when the patient changes.

Item 10: The computer program product of any one of the preceding Items, the operations further comprising: applying an edge detection algorithm to a radiation pattern present in the images, the edge detection algorithm determining at least one edge of the radiation pattern corresponding to a leaf of a multi-leaf collimator; and determining a leaf position based at least on a location of the determined edge.

Item 11: The computer program product of any one of the preceding Items, the operations further comprising comparing the leaf position with a planned leaf position, the comparing utilized in radiation therapy quality assurance.

Item 12: The computer program product of any one of the preceding Items, the operations further comprising calculating a fluence map based at least on the leaf position and beam output data obtained from the radiation therapy system.

Item 13: The computer program product of any one of the preceding Items, the operations further comprising calculating a dose at a target location based at least on the fluence map and a patient image obtained from an imaging system.

Item 14: The computer program product of any one of the preceding Items, wherein the dose is a three-dimensional dose delivered at the target location.

Item 15: A system comprising: at least one programmable processor; and a non-transitory machine-readable medium storing instructions which, when executed by the at least one programmable processor, cause the at least one programmable processor to perform operations comprising those of any of Items 1-14.

Item 16: A method performing operations as in any one of the preceding Items 1-14.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on,"

above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A computer program product comprising a non-transitory, machine-readable medium storing instructions which, when executed by at least one programmable processor, cause the at least one programmable processor to perform operations comprising:
   receiving a video stream;
   acquiring images capturing at least a portion of a shape representative of a radiation pattern generated by a radiation delivery system that includes a radiation source configured to deliver a radiation beam, wherein the acquiring is performed by extracting the images from the video stream.

2. The computer program product of claim 1, the operations further comprising:
   receiving, at a video encoder, a digital video signal output from a monitor associated with a radiation detector; and
   converting, with the video encoder, the digital video signal output to the video stream.

3. The computer program product of claim 1, the operations further comprising:
   receiving, at a video encoder, a digital video signal output from a radiation detector; and
   converting, with the video encoder, the digital video signal output to the video stream.

4. The computer program product of claim 3, the operations further comprising:
   transmitting the digital video signal output from the video encoder to a monitor associated with the radiation detector.

5. The computer program product of claim 1, wherein the video stream is received from a server that is not part of the radiation detector.

6. The computer program product of claim 5, the operations further comprising:
   generating a recorded video stream from the video stream obtained from the server,
   wherein the acquired images are obtained from the recorded video stream.

7. The computer program product of claim 1, the operations further comprising:
   generating a recorded video stream from the received video stream,
   wherein the acquired images are obtained from the recorded video stream.

8. The computer program product of claim 7, the operations further comprising:
   determining start and end points of the recorded video stream by analyzing the video stream to determine when the patient changes.

9. The computer program product of claim 1, the operations further comprising:
   applying an edge detection algorithm to a radiation pattern present in the images, the edge detection algorithm determining at least one edge of the radiation pattern corresponding to a leaf of a multi-leaf collimator; and
   determining a leaf position based at least on a location of the determined edge.

10. The computer program product of claim 9, the operations further comprising comparing the leaf position with a planned leaf position, the comparing utilized in radiation therapy quality assurance.

11. The computer program product of claim 10, the operations further comprising calculating a fluence map based at least on the leaf position and beam output data obtained from the radiation therapy system.

12. The computer program product of claim 11, the operations further comprising calculating a dose at a target location based at least on the fluence map and a patient image obtained from an imaging system.

13. The computer program product of claim 12, wherein the dose is a three-dimensional dose delivered at the target location.

14. A method comprising:
   receiving a video stream; and
   acquiring images from the video stream, the images capturing at least a portion of a shape representative of a radiation pattern generated by a radiation delivery system that includes a radiation source configured to deliver the radiation beam,
   wherein the acquiring is performed by extracting the images from the video stream.

15. The method of claim 14, further comprising:
   receiving, at a video encoder, a digital video signal output from a monitor associated with a radiation detector; and
   converting, with the video encoder, the digital video signal output to the video stream.

16. The method of claim 14, further comprising:
   receiving, at a video encoder, a digital video signal output from a radiation detector; and
   converting, with the video encoder, the digital video signal output to the video stream.

17. The method of claim 16, further comprising:
transmitting the digital video signal output from the video encoder to a monitor associated with the radiation detector.

18. The method of claim 14, wherein the video stream is received from a server that is not part of the radiation detector.

19. The method of claim 18, further comprising:
generating a recorded video stream from the video stream obtained from the server,
wherein the acquired images are obtained from the recorded video stream.

20. The method of claim 14, further comprising:
generating a recorded video stream from the received video stream,
wherein the acquired images are obtained from the recorded video stream.

21. The method of claim 20, further comprising:
determining start and end points of the recorded video stream by analyzing the video stream to determine when the patient changes.

\* \* \* \* \*